US012601006B2

(12) United States Patent
Song et al.

(10) Patent No.: US 12,601,006 B2
(45) Date of Patent: Apr. 14, 2026

(54) TARGETED, LONG-READ NUCLEIC ACID SEQUENCING FOR THE DETERMINATION OF CYTOSINE MODIFICATIONS

(71) Applicant: LUDWIG INSTITUTE FOR CANCER RESEARCH LTD, Zurich (CH)

(72) Inventors: Chunxiao Song, Oxford (GB); Yibin Liu, Oxford (GB)

(73) Assignee: Ludwig Institute for Cancer Research LTD., Zurich (CH)

( * ) Notice: Subject to any disclaimer, the term of this patent is extended or adjusted under 35 U.S.C. 154(b) by 869 days.

(21) Appl. No.: 17/929,033

(22) PCT Filed: Feb. 10, 2021

(86) PCT No.: PCT/IB2021/051091
§ 371 (c)(1),
(2) Date: Aug. 10, 2022

(87) PCT Pub. No.: WO2021/161192
PCT Pub. Date: Aug. 19, 2021

(65) Prior Publication Data
US 2023/0076949 A1      Mar. 9, 2023

Related U.S. Application Data

(60) Provisional application No. 62/972,986, filed on Feb. 11, 2020.

(51) Int. Cl.
*C12Q 1/6827* (2018.01)
(52) U.S. Cl.
CPC .................................. *C12Q 1/6827* (2013.01)
(58) Field of Classification Search
CPC .............................................. C12Q 2537/164
See application file for complete search history.

(56) References Cited

U.S. PATENT DOCUMENTS

| | | |
|---|---|---|
| 7,582,420 B2 | 9/2009 | Oliphant et al. |
| 8,741,567 B2 | 6/2014 | He et al. |
| 9,267,117 B2 | 2/2016 | Guan et al. |
| 10,155,939 B1 | 12/2018 | Vaisvila et al. |
| 11,306,355 B2 | 4/2022 | Song et al. |
| 2014/0127678 A1 | 5/2014 | Guan et al. |
| 2014/0322707 A1 | 10/2014 | He et al. |
| 2017/0176421 A1 | 6/2017 | Rao et al. |
| 2017/0253924 A1 | 9/2017 | Lu et al. |
| 2018/0171397 A1 | 6/2018 | Vaisvila et al. |
| 2018/0251815 A1 | 9/2018 | Okamoto et al. |
| 2020/0024643 A1 | 1/2020 | Arensdorf et al. |
| 2020/0370114 A1 | 11/2020 | Song et al. |
| 2022/0275424 A1 | 9/2022 | Song et al. |

FOREIGN PATENT DOCUMENTS

| | | | |
|---|---|---|---|
| EP | 2694686 | 11/2017 | |
| WO | WO 2013/017853 | 2/2013 | |
| WO | WO 2014/074450 | 5/2014 | |
| WO | WO 2014/083118 | 6/2014 | |
| WO | WO 2014/165770 | 10/2014 | |
| WO | WO 2015/021282 | 2/2015 | |
| WO | WO 2016/164363 | 10/2016 | |
| WO | WO 2017/039002 | 3/2017 | |
| WO | WO 2017/176630 | 10/2017 | |
| WO | WO 2019/136413 | 7/2019 | |
| WO | WO-2019136413 A1 * | 7/2019 | ..... C12Y 204/01027 |
| WO | WO-2019160994 A1 * | 8/2019 | .......... C12Q 1/6827 |
| WO | WO 2021/005537 | 1/2021 | |
| WO | WO 2022/053872 | 3/2022 | |

OTHER PUBLICATIONS

Liu et al. Nature Biotechnology. 2019. 37:424-429. (Year: 2019).*
Siejka-Zielinska. "Development of bisulfite-free DNA methylation sequencing methods and their application to cell-free DNA for cancer detection." Doctoral Thesis. University of Oxford. 2020. (Year: 2020).*
Liu et al. Cancer Res. 2019. 79(13 Supplement): 825 (Year: 2019).*
Liu et al. Genome Biology. 2020. 21:54. (Year: 2020).*
Ambrogelly et al., Screening of reducing agents for the PEGylation of recombinant human IL-10. Protein J. Jun. 2013;32(5):337-42.
Amemiya et al., The Encode Blacklist: Identification of Problematic Regions of the Genome. Sci Rep. Jun. 27, 2019;9(1):9354. 5 pages.
Aparici-Espert et al., A Combined Experimental and Theoretical Approach to the Photogeneration of 5,6-Dihydropyrimidin-5-yl Radicals in Nonaqueous Media. J Org Chem. May 20, 2016;81(10):4031-8.
Bachman et al., 5-Formylcytosine can be a stable DNA modification in mammals. Nat Chem Biol. Aug. 2015;11(8):555-7.
Bogu et al., Chromatin and RNA Maps Reveal Regulatory Long Noncoding RNAs in Mouse. Mol Cell Biol. Dec. 28, 2015;36(5):809-19.
Booth et al., Chemical methods for decoding cytosine modifications in DNA. Chem Rev. Mar. 25, 2015;115(6):2240-54.
Booth et al., Quantitative sequencing of 5-methylcytosine and 5-hydroxymethylcytosine at single-base resolution. Science. May 18, 2012;336(6083):934-7.
Chaurasia et al., Application of crude laccase of Xylaria polymorpha MTCC-1100 in selective oxidation of aromatic methyl group to aldehyde group. BCAIJ, 2012. 6(7), 237-242.
Chen et al., fastp: an ultra-fast all-in-one FASTQ preprocessor. Bioinformatics. Sep. 1, 2018;34(17):1884-i890.
Darst et al., Bisulfite sequencing of DNA. Curr Protoc Mol Biol. Jul. 2010;Chapter 7:Unit 7.9.1-17.

(Continued)

*Primary Examiner* — Joseph G. Dauner
(74) *Attorney, Agent, or Firm* — Casimir Jones, S.C.; J. Mitchell Jones

(57)            ABSTRACT

The present disclosure provides a bisulfite-free, long-read, base-resolution method named long-read TAPS (lrTAPS) for detecting 5-Methylcytosine (5mC) and 5-hydroxymethylcytosine (5hmC) in a nucleic acid sequence. lrTAPS comprises mild enzymatic and chemical reactions to detect 5mC and 5hmC, the two major epigenetic marks found in the mammalian genome, quantitatively at base-resolution without affecting unmodified cytosine.

13 Claims, 11 Drawing Sheets

Specification includes a Sequence Listing.

(56)　　　　　　References Cited

OTHER PUBLICATIONS

Dietzsch et al., Chemoselective labeling and site-specific mapping of 5-formylcytosine as a cellular nucleic acid modification. FEBS Lett. Jun. 2018;592(12):2032-2047.

Dizdaroglu et al., Substrate specificity of the *Escherichia coli* endonuclease III: excision of thymine- and cytosine-derived lesions in DNA produced by radiation-generated free radicals. Biochemistry. Nov. 16, 1993;32(45):12105-11.

Encode Project Consortium. An integrated encyclopedia of DNA elements in the human genome. Nature. Sep. 6, 2012;489(7414):57-74.

Ernst et al., ChromHMM: autmating chromatin-state discovery and characterization. Nat Methods. Feb. 28, 2012;9(3):215-6.

Extended European Search Report for PCT/US2019012627. Mailed Sep. 21, 2020. 9 pages.

GenBank—EMBL Accession No. J02459. Jan. 2020. 33 pages.

He et al., DeepH&M: Estimating single-CpG hydroxymethylation and methylation levels from enrichment and restriction enzyme sequencing methods. Sci Adv. Jul. 1, 2020;6(27):eaba0521. 11 pages.

He et al., Tet-mediated formation of 5-carboxylcytosine and its excision by TDG in mammalian DNA. Science. Sep. 2, 2011;333(6047):1303-7.

Holmes et al., Performance evaluation of kits for bisulfite-conversion of DNA from tissues, cell lines, FFPE tissues, aspirates, lavages, effusions, plasma, serum, and urine. PLoS One. Apr. 3, 2014;9(4):e93933. 15 pages.

House et al., Hydrolysis of dihydrouridine and related compounds. Biochemistry. Jan. 9, 1996;35(1):315-20.

Hu et al., Structural insight into substrate preference for TET-mediated oxidation. Nature. Nov. 5, 2015;527(7576):118-22.

Incarnato et al., High-throughput single nucleotide variant discovery in E14 mouse embryonic stem cells provides a new reference genome assembly. Genomics. Aug. 2014;104(2):121-7.

International Search Report for PCT/US2019/012627, Mailed May 7, 2019. 5 pages.

International Search Report and Written Opinion for PCT/IB2020/056435. Mailed Oct. 19, 2020 . 10 pages.

International Search Report and Written Opinion for PCT/IB2021/000630. Mailed Jan. 31, 2022. 21 pages.

International Search Report and Written Opinion for PCT/IB2021/051091; mailed Nov. 5, 2021; pp. 1-10.

International Search Report and Written Opinion, PCT/US2019/017902. Dated Apr. 11, 2019, 6 pages.

Ito et al., Tet proteins can convert 5-methylcytosine to 5-formylcytosine and 5-carboxylcytosine. Science. Sep. 2, 2011;333(6047):1300-3.

Iyer et al., Comparative genomics of transcription factors and chromatin proteins in parasitic protists and other eukaryotes. Int J Parasitol. Jan. 2008;38(1):1-31.

Jiang et al., Characterization of *Escherichia coli* endonuclease VIII. J Biol Chem. Dec. 19, 1997;272(51):32230-9.

Kellinger et al., 5-formylcytosine and 5-carboxylcytosine reduce the rate and substrate specificity of RNA polymerase II transcription. Nat Struct Mol Biol. Aug. 2012;19(8):831-3.

Kent et al., BigWig and BigBed: enabling browsing of large distributed datasets. Bioinformatics. Sep. 1, 2010;26(17):2204-7.

Kim et al., CTCF as a multifunctional protein in genome regulation and gene expression. Exp Mol Med. Jun. 5, 2015;47(6):e166. 5 pages.

Ko et al., Hepatitis B virus genome recycling and de novo secondary infection events maintain stable cccDNA levels. J Hepatol. Dec. 2018;69(6):1231-1241.

Kriaucionis et al. The nuclear DNA base 5-hydroxymethylcytosine is present in Purkinje neurons and the brain. Science. May 15, 2009;324(5929):929-30.

Krueger et al., Bismark: a flexible aligner and methylation caller for Bisulfite-Seq applications. Bioinformatics. Jun. 1, 2011;27(11):1571-2.

Kundaje et al., mod/mouse/humanEncode: Blacklisted genomic regions for functional genomics analysis. Stanford School of Medicine. 2014. 3 pages.

Langmead et al., Fast gapped-read alignment with Bowtie 2. Nat Methods. Mar. 4, 2012;9(4):357-9.

Li et al., DNA methylation in mammals. Cold Spring Harb Perspect Biol. May 1, 2014;6(5):a019133. 21 pages.

Li et al., Fast and accurate short read alignment with Burrows-Wheeler transform. Bioinformatics. Jul. 15, 2009;25(14):1754-60.

Li et al., The Sequence Alignment/Map format and SAMtools. Bioinformatics. Aug. 15, 2009;25(16):2078-9.

LI. Minimap2: pairwise alignment for nucleotide sequences. Bioinformatics. Sep. 15, 2018;34(18):3094-3100.

Liu et al., Accurate targeted long-read DNA methylation and hydroxymethylation sequencing with Taps. Genome Biol. Mar. 3, 2020;21(1):54. 9 pages.

Liu et al., Bisulfite-free direct detection of 5-methylcytosine and 5-hydroxymethylcytosine at base resolution. Nat Biotechnol. Apr. 2019;37(4):424-429.

Liu et al., Bisulfite-free, Base-resolution, and Quantitative Sequencing of CytosineModifications. bioRxiv, 2018. pp. 1-18.

Liu et al., DNA 5-Methylcytosine-Specific Amplification and Sequencing. J Am Chem Soc. Mar. 11, 2020;142(10):4539-4543.

Lu et al., Chemical modification-assisted bisulfite sequencing (CAB-Seq) for 5-carboxylcytosine detection in DNA. J Am Chem Soc. Jun. 26, 2013;135(25):9315-7.

Matsushita et al., DNA-friendly Cu(ii)/Tempo-catalyzed 5-hydroxymethylcytosine-specific oxidation. Chem Commun (Camb). May 23, 2017;53(42):5756-5759.

Meissner et al., Reduced representation bisulfite sequencing for comparative high-resolution DNA methylation analysis. Nucleic Acids Res. Oct. 13, 2005;33(18):5868-77.

Mellen et al., MeCP2 binds to 5hmC enriched within active genes and accessible chromatin in the nervous system. Cell. Dec. 21, 2012;151(7):1417-30.

Moriya et al., A novel modified nucleoside found at the first position of the anticodon of methionine tRNA from bovine liver mitochondria. Biochemistry. Mar. 1, 1994;33(8):2234-9.

Neri et al., Intragenic DNA methylation prevents spurious transcription initiation. Nature. Mar. 2, 2017;543(7643):72-77.

Nestor et al., Tissue type is a major modifier of the 5-hydroxymethylcytosine content of human genes. Genome Res. Mar. 2012;22(3):467-77.

Pais et al., Biochemical characterization of a Naegleria TET-like oxygenase and its application in single molecule sequencing of 5-methylcytosine. Proc Natl Acad Sci U S A. Apr. 7, 2015;112(14):4316-21.

Plongthongkum et al., Advances in the profiling of DNA modifications: cytosine methylation and beyond. Nat Rev Genet. Oct. 2014;15(10):647-61.

Ponnaluri et al., A mechanistic overview of TET-mediated 5-methylcytosine oxidation. Biochem Biophys Res Commun. Jun. 28, 2013;436(2):115-20.

Qu et al., MLML: consistent simultaneous estimates of DNA methylation and hydroxymethylation. Bioinformatics. Oct. 15, 2013;29(20):2645-6.

Quinlan et al., BEDTools: a flexible suite of utilities for comparing genomic features. Bioinformatics. Mar. 15, 2010;26(6):841-2.

Roberston et al., A novel method for the efficient and selective identification of 5-hydroxymethylcytosine in genomic DNA. Nucleic Acids Res. Apr. 2011;39(8):e55. pp. 1-10.

Robinson et al., Integrative genomics viewer. Nat Biotechnol. Jan. 2011;29(1):24-6.

Rosenbloom et al., Encode data in the UCSC Genome Browser: year 5 update. Nucleic Acids Res. Jan. 2013;41(Database issue):D56-63.

Ruhaak et al., 2-picoline-borane: a non-toxic reducing agent for oligosaccharide labeling by reductive amination. Proteomics. Jun. 2010;10(12):2330-6.

Schuler et al., Sequencing the sixth base (5-hydroxymethylcytosine): selective DNA oxidation enables base-pair resolution. Angew Chem Int Ed Engl. Oct. 22, 2012;51(43):10704-7.

(56)                 References Cited

OTHER PUBLICATIONS

Schutsky et al., Nondestructive, base-resolution sequencing of 5-hydroxymethylcytosine using a DNA deaminase. Nat Biotechnol. Oct. 8, 2018;10.1038/nbt.4204. 23 pages.

Shen et al., A map of the cis-regulatory sequences in the mouse genome. Nature. Aug. 2, 2012;488(7409):116-20.

Simpson et al., Detecting DNA cytosine methylation using nanopore sequencing. Nat Methods. Apr. 2017;14(4):407-410.

Song et al., 5-Hydroxymethylcytosine signatures in cell-free DNA provide information about tumor types and stages. Cell Res. Oct. 2017;27(10):1-12.

Song et al., Genome-wide profiling of 5-formylcytosine reveals its roles in epigenetic priming. Cell. Apr. 25, 2013;153(3):678-91.

Song et al., Selective chemical labeling reveals the genome-wide distribution of 5-hydroxymethylcytosine. Nat Biotechnol. Jan. 2011;29(1):68-72.

Song. Bisulfite-free, base resolution and quantitative identification of cytosine modifications. Keystone Symposia Conference, DNA & RNA Methylation, Ludwig Institute for Cancer Research, University of Oxford, Jan. 24, 2018, pp. 1-18.

Stoiber et al., De novo Identification of DNA Modifications Enabled by Genome-Guided Nanopore Signal Processing. bioRxiv,2017, pp. 1-28.

Tahiliani et al., Conversion of 5-methylcytosine to 5-hydroxymethylcytosine in mammalian DNA by MLL partner TET1. Science. May 15, 2009;324(5929):930-5.

Tanaka et al., Degradation of DNA by bisulfite treatment. Bioorg Med Chem Lett. Apr. 1, 2007;17(7):1912-5.

Therasse et. al., New guidelines to evaluate the response to treatment in solid tumors. European Organization for Research and Treatment of Cancer, National Cancer Institute of the United States, National Cancer Institute of Canada. J Natl Cancer Inst. Feb. 2, 2000;92(3):205-16.

Vaisvila et al., Enzymatic methyl sequencing detects DNA methylation at single-base resolution from picograms of DNA. Genome Res. Jun. 17, 2021;31(7):1280-1289.

Wang et al., Bisulfite-free, single base-resolution analysis of 5-hydroxymethylcytosine in genomic DNA by chemical-mediated mismatch. Chem Sci. Oct. 11, 2018;10(2):447-452.

Wen et al., Whole-genome analysis of 5-hydroxymethylcytosine and 5-methylcytosine at base resolution in the human brain. Genome Biol. Mar. 4, 2014;15(3):R49. 17 pages.

Written Opinion, PCT/US2019/012627. mailed May 7, 2019. 12 pages.

Wu et al., Base-resolution profiling of active DNA demethylation using MAB-seq and caMAB-seq. Nat Protoc. Jun. 2016;11(6):1081-100.

Xia et al., Bisulfite-free, base-resolution analysis of 5-formylcytosine at the genome scale. Nat Methods. Nov. 2015;12(11):1047-50.

Yu et al., Base-resolution analysis of 5-hydroxymethylcytosine in the mammalian genome. Cell. Jun. 8, 2012;149(6):1368-80.

Yu et al., Tet-assisted bisulfite sequencing of 5-hydroxymethylcytosine. Nat Protoc. Dec. 2012;7(12):2159-70.

Zeng et al., Bisulfite-Free, Nanoscale Analysis of 5-Hydroxymethylcytosine at Single Base Resolution. J Am Chem Soc. Oct. 17, 2018;140(41):13190-13194.

Zhao et al., Mapping the epigenetic modifications of DNA and RNA. Protein Cell. Nov. 2020;11(11):792-808.

Zhu et al., Single-Cell 5-Formylcytosine Landscapes of Mammalian Early Embryos and ESCs at Single-Base Resolution. Cell Stem Cell. May 4, 2017;20(5):720-731.e5.

Zuo et al., Oxidative damage to 5-methylcytosine in DNA. Nucleic Acids Research, 1995, vol. 23, No. 16, 3239-3243.

* cited by examiner

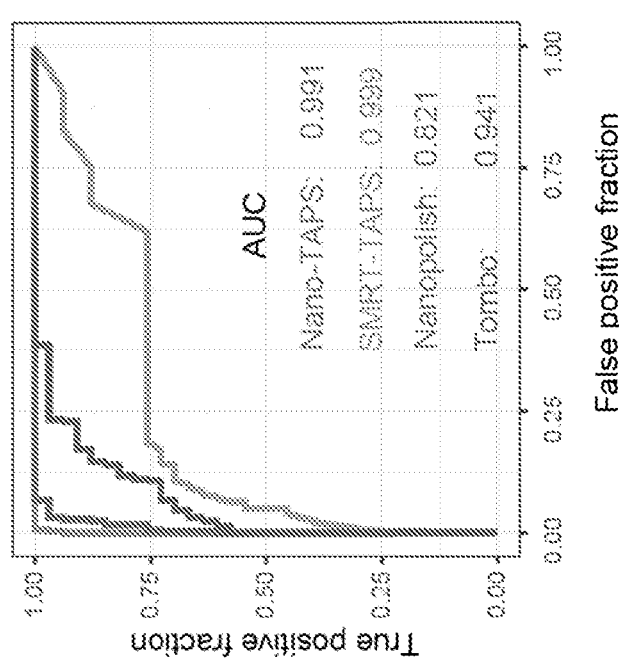
2B
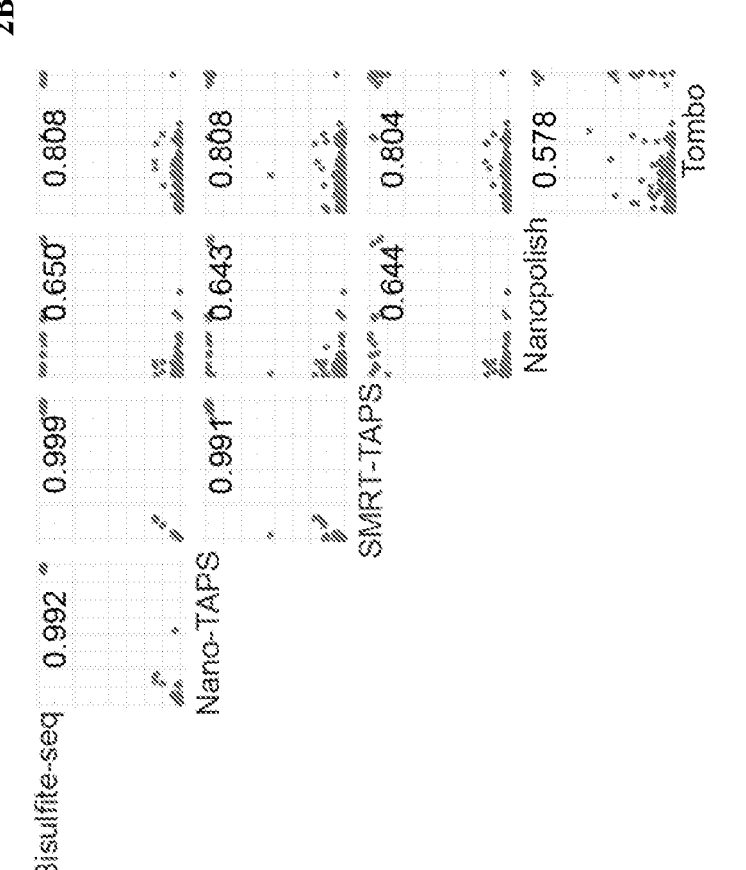
2A
Figure 2

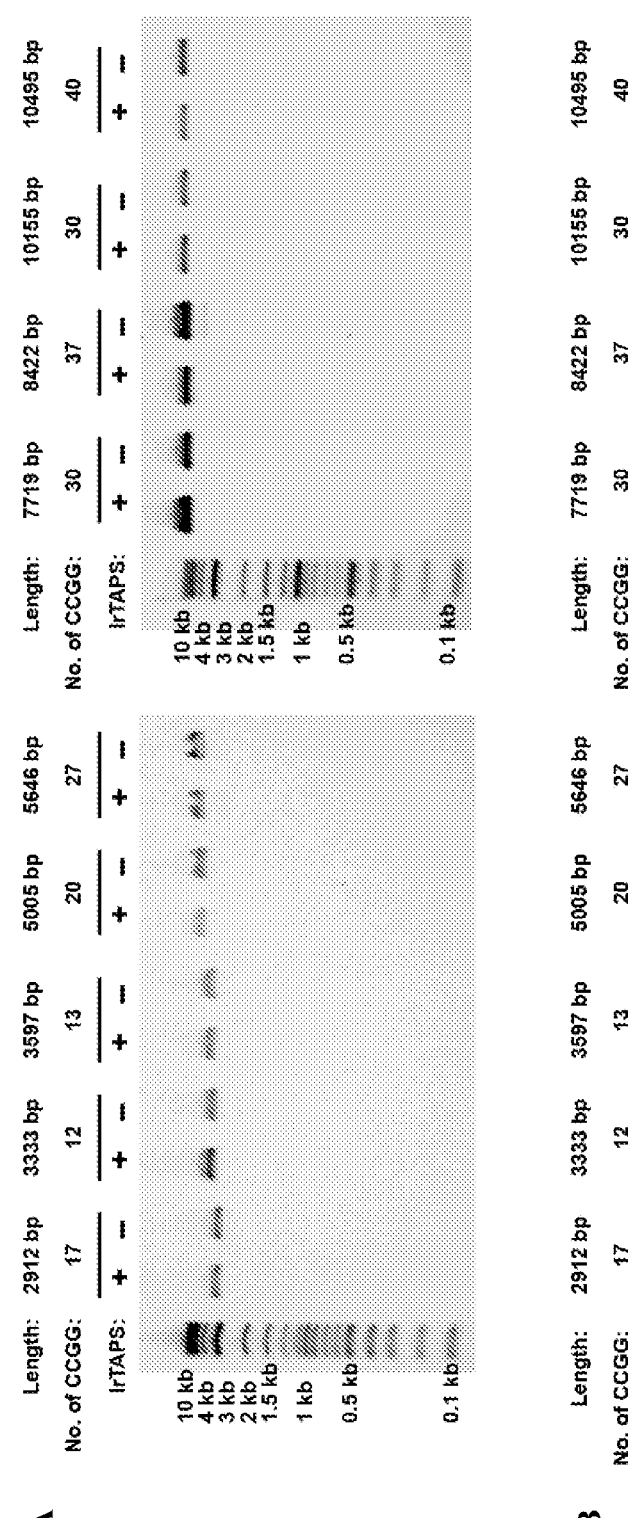
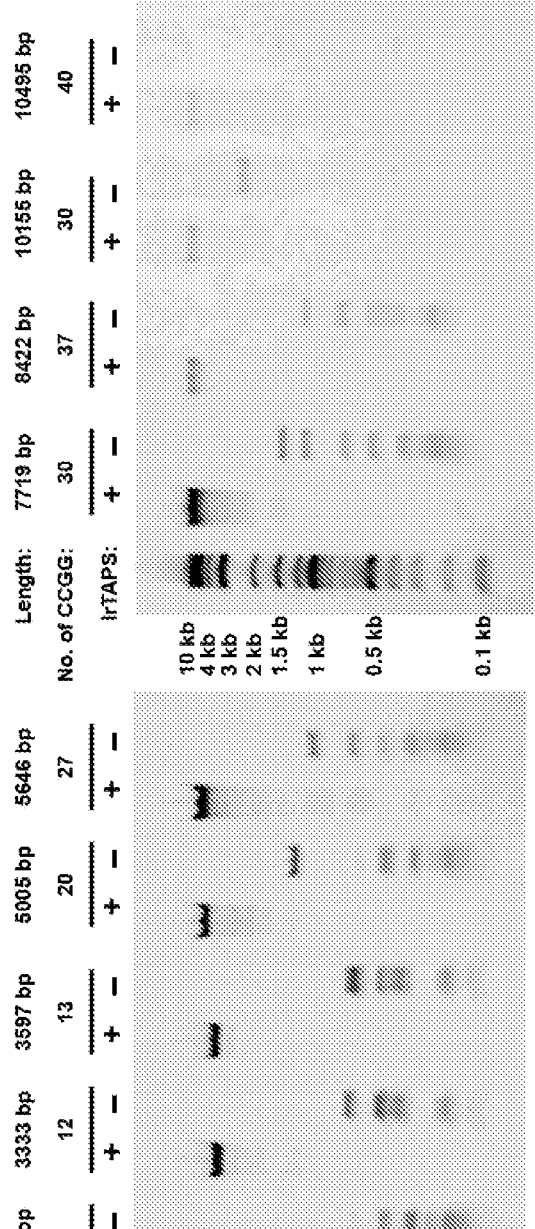
Figure 3

CLUSTAL O(1.2.4) multiple sequence alignment

```
Hba-a1::chr11:32183671-32184486    GACACTTCTGATTCTGACAGACTCAGGAAGAAACCATGGTGCTCTCTGGGGAAGACAAAA    60
Hba-a2::chr11:32196491-32197310    ---ACTTCTGATTCTGACAGACTCAGGAAGAAACCATGGTGCTCTCTGGGGAAGACAAAA    57
                                      ******************************************************

Hba-a1::chr11:32183671-32184486    GCAACATCAAGGCTGCCTGGGGGAAGATTGGTGGCCATGGTGCTGAATATGGAGCTGAAG    120
Hba-a2::chr11:32196491-32197310    GCAACATCAAGGCTGCCTGGGGGAAGATTGGTGGCCATGGTGCTGAATATGGAGCTGAAG    117
                                   ************************************************************

Hba-a1::chr11:32183671-32184486    CCCTGGAAAGGTGAGAACAGGACCTtgatctgtaaggatcacaggatccaatatggacct    180
Hba-a2::chr11:32196491-32197310    CCCTGGAAAGGTGAGAACAGGACCTtgatctgtaaggatcacaggatccaatatggacct    177
                                   ************************************************************

Hba-a1::chr11:32183671-32184486    ggcactcgCTCAGTGGGCAGCTTCTAACTATGCTTTTCTGTGACCTCAACTTCTCTTCTC    240
Hba-a2::chr11:32196491-32197310    ggcactcgCTCAGTGGGCAGCTTCTAACTATGCTTTTCTGTGACCTCAACTTCTCTTCTC    237
                                   ************************************************************

Hba-a1::chr11:32183671-32184486    TCCTTCTCCCAGGATGTTTGCTAGCTTCCCCACCACCAAGACCTACTTCCCTCACTTTGA    300
Hba-a2::chr11:32196491-32197310    TCCTTCTCCCAGGATGTTTGCTAGCTTCCCCACCACCAAGACCTACTTCCCTCACTTTGA    297
                                   ************************************************************

Hba-a1::chr11:32183671-32184486    TGTAAGCCACGGCTCTGCCCAGGTCAAGGGTCACGGCAAGAAGGTCGCCGATGCTCTGGC    360
Hba-a2::chr11:32196491-32197310    TGTAAGCCACGGCTCTGCCCAGGTCAAGGGTCACGGCAAGAAGGTCGCCGATGCTCTGGC    357
                                   ************************************************************

Hba-a1::chr11:32183671-32184486    CAATGCTGCAGGCCACCTCGATGACCTGCCCGGTGCCCTGTCTGCTCTGAGCGACCTGCA    420
Hba-a2::chr11:32196491-32197310    CAATGCTGCAGGCCACCTCGATGACCTGCCCGGTGCCCTGTCTGCTCTGAGCGACCTGCA    417
                                   ************************************************************

Hba-a1::chr11:32183671-32184486    TGCCCACAAGCTGCGTGTGGATCCCGTCAACTTCAAGGTATGCGCTGGGACCTGGCAGGC    480
Hba-a2::chr11:32196491-32197310    TGCCCACAAGCTGCGTGTGGATCCCGTCAACTTCAAGGTATGCGCTGGGACCTGGCAGGC    477
                                   ************************************************************

Hba-a1::chr11:32183671-32184486    GGCATCTGGGACCCCTAGGAAGGGCTTGGGGGTCCTCGTCGCCCAAGGCAGGGAACATAGT    540
Hba-a2::chr11:32196491-32197310    GGCATCTGGGACCCCTAGGAAGGGCTTGGGGGTCCTCGTCGCCCAAGGCAGGGAACATAGT    537
                                   ************************************************************

Hba-a1::chr11:32183671-32184486    GGTCCCAGGAAGGGGAGCAGAGGCATCAGGGTGTCCACTTTGTCTCCGCAGCTCCTGAGC    600
Hba-a2::chr11:32196491-32197310    GGTCCCAGGAAGGGGAGCAGAGGCATCAGGGTGTCCACTTTGTCTCCGCAGCTCCTGAGC    597
                                   ************************************************************

Hba-a1::chr11:32183671-32184486    CACTGCCTGCTGGTGACCTTGGCTAGCCACCACCCTGCCGATTTCACCCCCGCGGTGCAT    660
Hba-a2::chr11:32196491-32197310    CACTGCCTGCTGGTGACCTTGGCTAGCCACCACCCTGCCGATTTCACCCCCGCGGTGCAT    657
                                   ************************************************************

Hba-a1::chr11:32183671-32184486    GCCTCTCTGGACAAATTCCTTGCCTCTGTGAGCACCGTGCTGACCTCCAAGTACCGTTAA    720
Hba-a2::chr11:32196491-32197310    GCCTCTCTGGATAAATTCCTTGCCTCTGTGAGCACCGTGCTGACCTCCAAGTACCGTTAA    717
                                   *********** ************************************************

Hba-a1::chr11:32183671-32184486    GCTGCCTTCTGCGGGGCTTGCCTTCTGGCCATGCCCTTCTTCTCTCCCTTGCACCTGTAC    780
Hba-a2::chr11:32196491-32197310    GCTGCCTTCTGCGGGGCTTGCCTTCTGGCCATGCCCTTCTTCTCTCCCTTGCACCTGTAC    777
                                   ************************************************************

Hba-a1::chr11:32183671-32184486    CTCTTGGTCTTTGAATAAAGCCTGAGTAGGAAGAA-------    815
Hba-a2::chr11:32196491-32197310    CTCTTGGTCTTTGAATAAAGCCTGAGTAGGAAGAAGCCTGCA    819
                                   ***********************************
```

Figure 6

TARGETED, LONG-READ NUCLEIC ACID SEQUENCING FOR THE DETERMINATION OF CYTOSINE MODIFICATIONS

CROSS-REFERENCE TO RELATED APPLICATIONS

This application claims priority under 35 U.S.C. § 119(e) to U.S. Provisional Patent Application Ser. No. 62/972,986, filed Feb. 11, 2020, which is hereby incorporated by reference in its entirety.

FIELD OF THE INVENTION

This disclosure provides methods for identifying in a nucleic acid sequence the locations of 5-methylcytosine and 5-hydroxymethylcytosine.

BACKGROUND

5-Methylcytosine (5mC) and 5-hydroxymethylcytosine (5hmC) are the two major epigenetic marks found in the mammalian genome. 5hmC is generated from 5mC by the ten-eleven translocation (TET) family dioxygenases. Tet can further oxidize 5hmC to 5-formylcytosine (5fC) and 5-car-boxylcytosine (5caC), which exists in much lower abundance in the mammalian genome compared to 5mC and 5hmC (10-fold to 100-fold lower than that of 5hmC). Together, 5mC and 5hmC play crucial roles in a broad range of biological processes from gene regulation to normal development. Aberrant DNA methylation and hydroxymethylation have been associated with various diseases and are well-accepted hallmarks of cancer. Therefore, the determination of 5mC and 5hmC in DNA sequence is not only important for basic research, but also is valuable for clinical applications, including diagnosis and therapy.

5fC and 5caC are the two final oxidized derivatives of 5mC and can be converted to unmodified cytosine by Thymine DNA glycosylase (TDG) in base excision repair pathway. Therefore, 5fC and 5caC are two key intermediates in the active demethylation process, which play important roles in embryonic development. 5fC and 5caC are found in these contexts and may serve as indicator of nearly complete 5mC demethylation. 5fC and 5caC may also play additional functions such as binding specific proteins and affecting the rate and specificity of RNA polymerase II.

5mC is also a post-transcriptional RNA modification that has been identified in both stable and highly abundant tRNAs and rRNAs, and in mRNAs. In addition, 5mC has been detected in snRNA (small nuclear RNA), miRNA (microRNA), lncRNA (long noncoding RNA) and eRNA (enhancer RNA). However, there appears to be differences in the occurrence of 5mC in specific RNA types in different organisms. For example, 5mC appears not to be present in tRNA and mRNA from bacteria, while it has been found in tRNA and mRNA in eukaryotes and archaea.

5hmC has also been detected in RNA. For example, mRNA from *Drosophila* and mouse has been found to contain 5hmC. The same family of enzymes that oxidize 5mC in DNA was reported to catalyze the formation of 5hmC in mammalian total RNA. In flies, a transcriptome wide study using methylation RNA immunoprecipitation sequencing (MeRIP-seq) with 5hmC antibodies, detected the presence of 5hmC in many mRNA coding sequences, with particularly high levels in the brain. It was also reported that active translation is associated with high 5hmC levels in RNA, and flies lacking the TET enzyme responsible for 5hmC deposition in RNA have impaired brain development.

Recent advances in third-generation sequencing methods, including PacBio Single-Molecule Real-Time (SMRT) sequencing and Oxford Nanopore sequencing, have enabled long-read and single-molecule sequencing that are distinct from the mainstream short-read Illumina sequencing. These newer sequencing platforms allow unambiguous mapping of repetitive and complex regions of the genome and provide opportunities for detecting structural variants, phasing haplotypes and assembling genomes. While Nanopore sequencing still has a high error rate (~10%), the latest SMRT sequencing provides accuracy similar to Illumina sequencing (99.8%) but with an average read length of 13.5 kilobase (kb) compared to ~0.3 kb with Illumina.

Long-read sequencing of DNA modifications, particularly the two abundant modifications 5-methylcytosine (5mC) and 5-hydroxymethylation (5hmC), is needed to obtain phased epigenomes that will enable new understanding of the functions of epigenetic modifications, for example allele-specific methylation in genomic imprinting and heterogeneous cancer samples, and diagnosis of brain tumors. Although the SMRT and Nanopore platforms can detect DNA modifications directly, there are major barriers to their application. SMRT sequencing can directly detect DNA modifications using polymerase kinetics information, but requires a minimum of 250× per strand coverage to detect 5-methylcytosine (5mC), largely defeating the purpose of long-read sequencing.

Several computational methods have been developed to detect base modifications directly from Oxford Nanopore sequencing. However, these approaches require complicated training data from control DNA samples of known methylation status and sophisticated computational analysis, limiting their accuracy to determine 5mC. Moreover, both native SMRT and Oxford Nanopore DNA methylation sequencing require microgram levels of native, unamplified DNA as input. Since amplification will erase any modifications, the application of these techniques on low-input samples, such as clinical materials, is limited. Moreover, conventional bisulfite sequencing (BS-seq), which yields the sum of 5mC and 5hmC, is intrinsically difficult with long-read sequencing due to severe DNA degradation caused by bisulfite treatment, which limits read length of SMRT-BS to ~1.5 kb.

There is a need for a convenient, long-read, sensitive, and accurate method for determining cytosine modifications in DNA molecules that can detect the modified cytosine (5mC and 5hmC) at base-resolution quantitatively without affecting the unmodified cytosine and that simplifies methylation detection on both SMRT and Nanopore sequencing platform.

SUMMARY OF THE INVENTION

Provided herein are methods for identifying the location of 5-methylcytosine (5mC) and/or 5-hydroxymethylcytosine (5hmC) in a nucleic acid. The disclosed methods allow accurate, long-read, cost-effective analysis of nucleic acid methylation using as low as nanogram quantities of input nucleic acid. The methods disclosed herein allow detection of modifications directly with high sensitivity and specificity, without affecting unmodified cytosines, and can be adopted to detect other cytosine modifications. Further, the disclosed methods are non-destructive, preserving RNA and DNA up to 10 kbs long. Compared with bisulfite sequencing, the disclosed methods result in higher mapping rates, more even coverage and lower sequencing costs, enabling higher quality, more comprehensive and cheaper methylome analyses. In addition, the methods disclosed herein can be used for analyzing allele-specific methylation.

In one aspect, the present disclosure provides a method for identifying 5-methylcytosine (5mC) in a target nucleic acid comprising the steps of:

a. providing a nucleic acid sample comprising the target nucleic acid;
 b. modifying the nucleic acid comprising the steps of:
  i. adding a blocking group to the 5-hydroxymethylcy-tosine (5hmC) in the nucleic acid sample;
  ii. converting the 5mC in the nucleic acid sample to 5-carboxylcytosine (5caC) and/or 5-formylcytosine (5fC); and
  iii. converting the 5caC and/or 5fC to dihydrouracil (DHU) to provide a modified nucleic acid sample comprising a modified target nucleic acid; and
 c. detecting the sequence of the modified target nucleic acid comprising detecting the presence of DHU in the sequence, or converting the DHU to thymine (T) and detecting the presence of the thymine (T) in the sequence;
  wherein a cytosine (C) to DHU transition or a cytosine (C) to thymine (T) transition in the sequence of the modified target nucleic acid compared to the target nucleic acid provides the location of a 5mC in the target nucleic acid;
 wherein steps ii and iii are performed in a single tube and/or without a purification step between steps ii and iii.

In some embodiments, steps i, ii, and iii are performed in a single tube and/or without a purification step between steps i, ii, and iii.

In embodiments of the method for identifying 5mC in a target nucleic acid, the percentages of a DHU or T at each transition location provide a quantitative level of 5mC at each location in the target nucleic acid. In embodiments, the step of adding a blocking group to the 5-hydroxymethylcy-tosine (5hmC) in the nucleic acid sample comprises contacting the nucleic acid sample with an enzyme, for example a β-glucosyltransferase. In embodiments, the step of converting the 5mC in the nucleic acid sample to 5-carboxyl-cytosine (5caC) and/or 5-formylcytosine (5fC) comprises contacting the nucleic acid with an enzyme, for example a TET enzyme. In embodiments, the method further comprises inactivating the one or more enzymes by providing a protease, by a change in temperature, and/or by a change in pH. In one embodiment, the protease is proteinase K. In some embodiments, the step of inactivating the one or more enzymes occurs between steps i. and ii. and/or between steps ii. and iii. In embodiments, the nucleic acid is DNA. In other embodiments, nucleic acid is RNA.

In another aspect, the present invention provides a method for identifying 5mC or 5hmC in a target nucleic acid comprising the steps of:

a. providing a nucleic acid sample comprising the target nucleic acid;
 b. modifying the nucleic acid comprising the steps of:
  i. converting the 5mC and 5hmC in the nucleic acid sample to 5-carboxylcytosine (5caC) and/or 5fC; and
  ii. converting the 5caC and/or 5fC to DHU to provide a modified nucleic acid sample comprising a modi-fied target nucleic acid; and
 c. detecting the sequence of the modified target nucleic acid comprising detecting the presence of DHU in the sequence, or converting the DHU to thymine (T) and detecting the presence of the thymine (T) in the sequence;
  wherein a cytosine (C) to DHU transition or a cytosine (C) to thymine (T) transition in the sequence of the modified target nucleic acid compared to the target nucleic acid provides the location of either a 5mC or 5hmC in the target nucleic acid;
  wherein steps i and ii are performed in a single tube and/or without a purification step between steps i and ii.

In embodiments of the method for identifying 5mC or 5hmC, the percentages of a DHU or T at each transition location provide a quantitative level of 5mC or 5hmC at each location in the target nucleic acid. In embodiments, the step of converting the 5mC and 5hmC in the nucleic acid sample to 5-carboxylcytosine (5caC) and/or 5fC comprises contact-ing the nucleic acid with an enzyme, for example a TET enzyme. In embodiments, the method further comprises inactivating the enzyme by providing a protease, by a change in temperature, and/or by a change in pH. In one embodiment, the protease is proteinase K. In some embodi-ments, the step of inactivating the enzyme occurs between steps i and ii. In embodiments, the nucleic acid is DNA. In other embodiments, nucleic acid is RNA.

In another aspect, the invention provides a method for identifying 5mC and identifying 5hmC in a target nucleic acid comprising:

a. identifying 5mC in the target nucleic acid comprising the steps of:
  i. providing a first nucleic acid sample comprising the target nucleic acid;
  ii. modifying the nucleic acid in the first sample com-prising the steps of:
   1. adding a blocking group to the 5-hydroxymethyl-cytosine (5hmC) in the first nucleic acid sample;
   2. converting the 5mC in the first nucleic acid sample to 5caC and/or 5fC; and
   3. converting the 5caC and/or 5fC to DHU to provide a modified first DNA sample comprising a modi-fied target nucleic acid, wherein steps 2 and 3 are performed in a single tube and/or without a puri-fication step between steps 2 and 3, or wherein steps 1, 2, and 3 are performed in a single tube and/or without a purification step between steps 1, 2 and 3;
  iii. detecting the sequence of the modified target nucleic acid comprising detecting the presence of DHU in the sequence, or converting the DHU to thymine (T) and detecting the presence of the thymine (T) in the sequence; wherein a cytosine (C) to DHU transition or a cytosine (C) to thymine (T) transition in the sequence of the modified target nucleic acid com-pared to the target nucleic acid provides the location of a 5mC in the target nucleic acid.
 b. identifying 5mC or 5hmC in the target nucleic acid comprising the steps of:
  i. providing a second nucleic acid sample comprising the target nucleic acid;
  ii. modifying the nucleic acid in the second sample comprising the steps of:
   1. converting the 5mC and 5hmC in the second nucleic acid sample to 5caC and/or 5fC; and
   2. converting the 5caC and/or 5fC to DHU to provide a modified second nucleic acid sample comprising a modified target nucleic acid, wherein steps 1 and 2 are performed in a single tube and/or without a purification step between steps 1 and 2;

iii. detecting the sequence of the modified target nucleic acid from the second sample comprising detecting the presence of DHU in the sequence, or converting the DHU to thymine (T) and detecting the presence of the thymine (T) in the sequence; wherein a cytosine (C) to DHU transition or a cytosine (C) to thymine (T) transition in the sequence of the modified target nucleic acid compared to the target nucleic acid provides the location of either a 5mC or 5hmC in the target nucleic acid; and c. comparing the results of steps (a) and (b), wherein a C to DHU or C to T transition present in step (b) but not in step (a) provides the location of 5hmC in the target nucleic acid.

In embodiments for identifying 5mC and identifying 5hmC in a target nucleic acid, in step (a) the percentages of a DHU or T at each transition location provide a quantitative level of 5mC in the target nucleic acid; in step (b), the percentages of a DHU or T at each transition location provide a quantitative level of 5mC or 5hmC in the target nucleic acid; and in step (c) the differences in percentages for a C to DHU or T transition identified in step (b), but not in step (a) provides the quantitative level of a 5hmC at each location in the target nucleic acid.

In embodiments, the step of adding a blocking group to the 5-hydroxymethylcytosine (5hmC) in the first nucleic acid sample comprises contacting the first nucleic acid with an enzyme, for example a β-glucosyltransferase. In embodiments, the step of converting the 5mC in the first nucleic acid sample to 5caC and/or 5fC comprises contacting the first nucleic acid with an enzyme. In embodiments, the step of converting the 5mC and 5hmC in the second nucleic acid sample to 5caC and/or 5fC comprises contacting the second nucleic acid with an enzyme, for example a TET enzyme. In embodiments, the method further comprises inactivating the one or more enzymes by providing a protease, by a change in temperature, and/or by a change in pH. In one embodiment, the protease is proteinase K. In some embodiments, the step of inactivating the one or more enzymes during the step of modifying the nucleic acid in the first sample occurs between steps (1) and (2) and/or between steps (2) and (3). In some embodiments, the method is performed without a purification step between steps (2) and (3). In some embodiments, the step of inactivating the enzyme during the step of modifying the nucleic acid in the second sample occurs between steps (1) and (2). In embodiments, the nucleic acid is DNA. In other embodiments, nucleic acid is RNA.

In embodiments of the invention, the blocking group added to 5hmC in the nucleic acid sample is a sugar. In embodiments, the sugar is a naturally-occurring sugar or a modified sugar, for example glucose or a modified glucose. In embodiments of the invention, the blocking group is added to 5hmC by contacting the nucleic acid sample with uridine diphosphate (UDP) linked to a sugar, for example UDP-glucose or UDP linked to a modified glucose in the presence of a glucosyltransferase enzyme, for example, T4 bacteriophage β-glucosyltransferase (βGT) and T4 bacteriophage α-glucosyltransferase (αGT) and derivatives and analogs thereof.

In embodiments of the invention, the step of converting the 5mC in the nucleic acid sample to 5caC and/or 5fC and the step of converting the 5mC and 5hmC in the nucleic acid sample to 5caC and/or 5fC each comprises contacting the nucleic acid sample with a ten eleven translocation (TET) enzyme. In further embodiments, the TET enzyme is one or more of human TET1, TET2, and TET3; murine Tet1, Tet2, and Tet3; *Naegleria* TET (NgTET); *Coprinopsis cinerea* (CcTET) and derivatives or analogues thereof. In embodiments, the TET enzyme is NgTET or murine TET. In other embodiments, the TET enzyme is human TET1 (hTET1) or human TET2 (hTET2).

In embodiments, the location of 5caC or 5fC can be identified, in order, e.g., to subtract those positions from the results of the long-read methods described herein. In such embodiments, the method for identifying 5caC or 5fC in a target nucleic acid comprises the steps of:

a. providing a nucleic acid sample comprising the target nucleic acid;

b. converting the 5caC and 5fC to DHU to provide a modified nucleic acid sample comprising a modified target nucleic acid;

c. optionally amplifying the copy number of the modified target nucleic acid; and d. detecting the sequence of the modified target nucleic acid; wherein a cytosine (C) to thymine (T) transition in the sequence of the modified target nucleic acid compared to the target nucleic acid provides the location of either a 5caC or 5fC in the target nucleic acid.

In embodiments of the method for identifying 5caC or 5fC in a target nucleic acid, the percentages of the T at each transition location provide a quantitative level for 5caC or 5fC at each location in the target nucleic acid.

In embodiments, the step of converting the 5caC and/or 5fC to DHU comprises contacting the nucleic acid sample with a reducing agent, such as a borane reducing agent, including, for example, pyridine borane, 2-picoline borane (pic-BH₃), borane, sodium borohydride, sodium cyanoborohydride, and sodium triacetoxyborohydride. In a preferred embodiment, the reducing agent is pic-BH₃ and/or pyridine borane.

In embodiments, the methods above further comprise the step of amplifying the copy number of the modified target nucleic acid. In embodiments, this amplification step is performed prior to the step of detecting the sequence of the modified target nucleic acid. The step of amplifying the copy number when the modified target nucleic acid is DNA may be accomplished by performing the polymerase chain reaction (PCR), primer extension, and/or cloning. When the modified target nucleic acid is RNA, the step of amplifying the copy number may be accomplished by RT-PCR using oligo(dT) primer (for mRNA), random primers, and/or gene specific primers.

In embodiments, the DNA sample comprises picogram quantities of DNA. In embodiments of the invention, the DNA sample comprises about 1 pg to about 900 pg DNA, about 1 pg to about 500 pg DNA, about 1 pg to about 100 pg DNA, about 1 pg to about 50 pg DNA, about 1 to about 10 pg, DNA, less than about 200 pg, less than about 100 pg DNA, less than about 50 pg DNA, less than about 20 pg DNA, and less than about 5 pg DNA. In other embodiments of the invention, the DNA sample comprises nanogram quantities of DNA. In embodiments of the invention, the DNA sample contains about 1 to about 500 ng of DNA, about 1 to about 200 ng of DNA, about 1 to about 100 ng of DNA, about 1 to about 50 ng of DNA, about 1 ng to about 10 ng of DNA, about 1 ng to about 5 ng of DNA, less than about 100 ng of DNA, less than about 50 ng of DNA less than about 5 ng of DNA, or less that about 2 ng of DNA. In embodiments of the invention, the DNA sample comprises circulating cell-free DNA (cfDNA). In embodiments of the invention the DNA sample comprises microgram quantities of DNA.

In embodiments, the step of determining the sequence of the modified target nucleic acid comprises a long-read sequencing technology including PacBio Single-Molecule Real-Time (SMRT) sequencing and Oxford Nanopore sequencing.

BRIEF DESCRIPTION OF THE FIGURES

FIGS. 2A and 2B illustrates pairwise correlations between different sequencing methods. 2A. Scatter plots showing all pairwise correlations of all CpG sites among Nano-TAPS, SMRT-TAPS, native Nanopore methylation calling (Nanopolish and Tombo), and BS-seq, with correlation coefficient showing on top of each plot. 2B. ROC curve and AUC comparing Nano-TAPS, SMRT-TAPS and native Nanopore methylation sequencing (Nanopolish and Tombo), using DNA methylation from bisulfite sequencing (methylation level>3% was designated as methylated) as the truth.

FIGS. 3A and 3B illustrate the validation of lrTAPS by HpaII digestion. Images of 1% Agarose gel analysis of PCR products of lambda model DNA, using primers listed in Table 1 before (FIG. 3A) and after (FIG. 3B) HpaII digestion, and with (+) or without (−) lrTAPS conversion. The experiment was performed once.

FIG. 6 shows a sequence alignment of Hba-a1 (SEQ ID NO:25) and Hba-a2 (SEQ ID NO: 26). Sequences of Hba-a1 and Hba-a2 were extracted based on mm9 genome and annotation download from the world wide web at hgdownload.soe.ucsc.edu/goldenPath/mm9/database/ref-Gene.txt.gz.

DETAILED DESCRIPTION OF THE INVENTION

Figure 1:
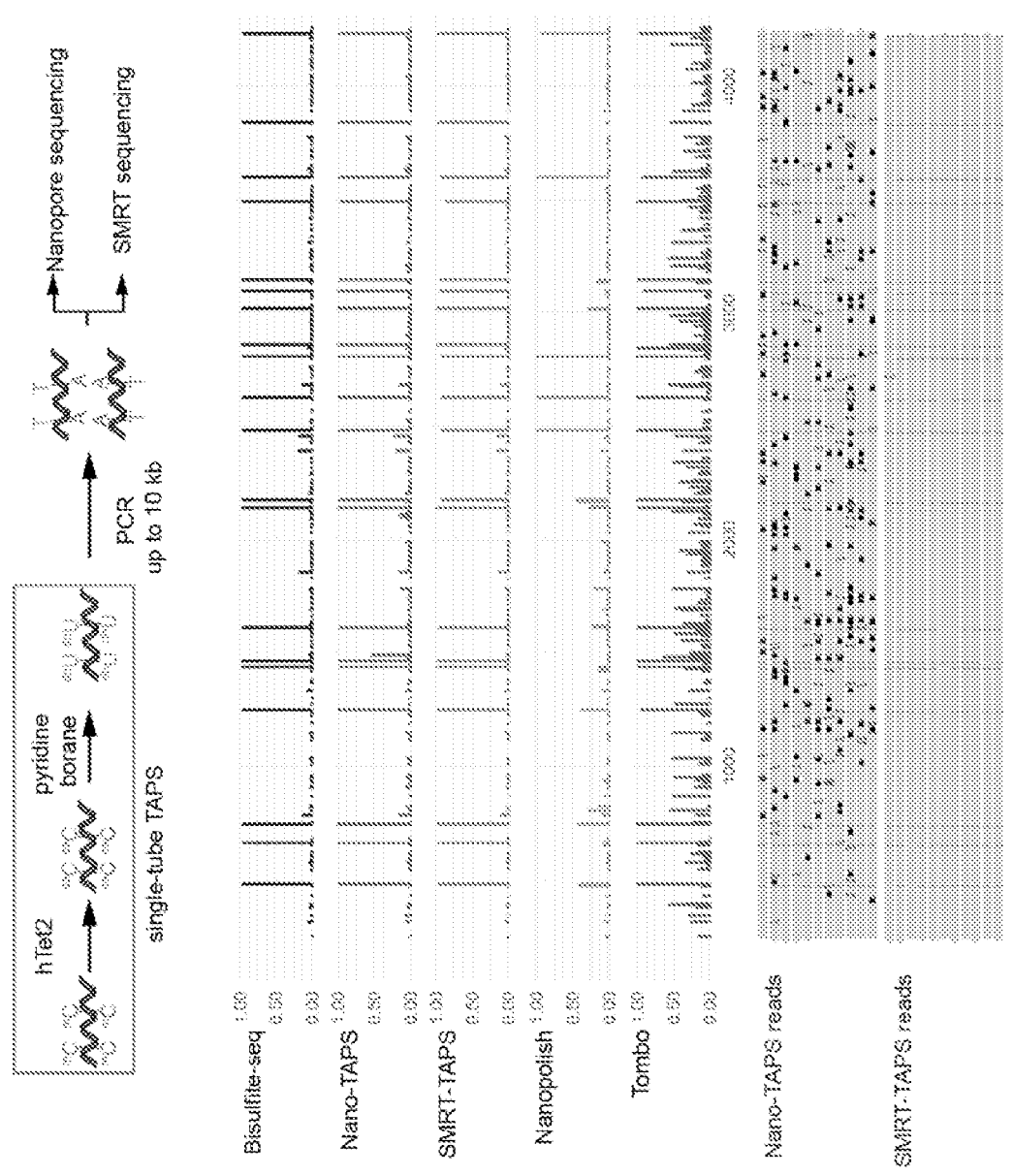
FIGS. 1A and 1B illustrate that long-read TAPS (lrTAPS) can be used to detect 5mC with high sensitivity and specificity. 1A. Schematic of lrTAPS for targeted long-read DNA methylation sequencing. 1B. Upper panel (from top to bottom): Methylation of a 4 kb model DNA obtained from bisulfite sequencing (short-read Illumina sequencing), Nano-TAPS, SMRT-TAPS, and native Nanopore methylation sequencing using Nanopolish or Tombo. The lower panel shows examples of individual long-reads from Nano-TAPS and SMRT-TAPS. Red bars indicate methylation. Black and purple bars indicate sequencing errors (deletions and insertions, respectively).

The present disclosure provides a bisulfite-free, long-read, base-resolution method for detecting 5mC and 5hmC in a nucleic acid sequence, herein named lrTAPS. lrTAPS comprises mild enzymatic and chemical reactions to detect 5mC and 5hmC directly and quantitatively at base-resolution without affecting unmodified cytosine. Thus, the methods provided herein provide mapping of 5mC and 5hmC and overcome the disadvantages of previous methods such as bisulfite sequencing.

Methods for Identifying 5mC

In one aspect, the present disclosure provides a method for identifying 5-methylcytosine (5mC) in a target nucleic acid comprising the steps of:
  a. providing a nucleic acid sample comprising the target nucleic acid;
  b. modifying the nucleic acid comprising the steps of:
    i. adding a blocking group to the 5-hydroxymethylcytosine (5hmC) in the nucleic acid sample;
    ii. converting the 5mC in the nucleic acid sample to 5-carboxylcytosine (5caC) and/or 5-formylcytosine (5fC); and
    iii. converting the 5caC and/or 5fC to dihydrouracil (DHU) to provide a modified nucleic acid sample comprising a modified target nucleic acid; and
  c. detecting the sequence of the modified target nucleic acid comprising detecting the presence of DHU in the sequence, or converting the DHU to thymine (T) and detecting the presence of the thymine (T) in the sequence;
    wherein a cytosine (C) to DHU transition or a cytosine (C) to thymine (T) transition in the sequence of the modified target nucleic acid compared to the target nucleic acid provides the location of a 5mC in the target nucleic acid,
    wherein steps ii and iii are performed in a single tube and/or without a purification step between steps ii and iii.

In some embodiments, steps i, ii, and iii are performed in a single tube and/or without a purification step between steps i, ii, and iii. In embodiments of the method for identifying 5mC in the target nucleic acid, the method provides a quantitative measure for the frequency the of 5mC modification at each location where the modification was identified in the target nucleic acid. In embodiments, the percentages of a DHU or T at each transition location provide a quantitative level of 5mC at each location in the target nucleic acid.

In some embodiments, the two or three of the step of adding a blocking group to the 5-hydroxymethylcytosine (5hmC) in the nucleic acid sample, the step of converting the 5mC in the nucleic acid sample to 5-carboxylcytosine (5caC) and/or 5-formylcytosine (5fC), and the step of converting the 5caC and/or 5fC to dihydrouracil (DHU) to provide a modified nucleic acid sample comprising a modified target nucleic acid are performed in the same tube or reaction vessel.

In order to identify 5mC in a target nucleic acid without including 5hmC, the 5hmC in the sample is blocked so that it is not subject to conversion to 5caC and/or 5fC. For example, 5hmC in the sample nucleic acid can be rendered non-reactive to the subsequent steps by adding a blocking group to the 5hmC. In one embodiment, the blocking group is a sugar, including a modified sugar, for example glucose or 6-azide-glucose (6-azido-6-deoxy-D-glucose). The sugar blocking group can be added to the hydroxymethyl group of 5hmC by contacting the nucleic acid sample with uridine diphosphate (UDP)-sugar in the presence of a glucosyltransferase enzyme.

In embodiments, the glucosyltransferase is T4 bacteriophage β-glucosyltransferase (βGT), T4 bacteriophage α-glucosyltransferase (αGT), and derivatives and analogs thereof. βGT is an enzyme that catalyzes a chemical reaction in which a beta-D-glucosyl (glucose) residue is transferred from UDP-glucose to a 5-hydroxymethylcytosine residue in a nucleic acid.

By stating that the blocking group is, for example, glucose, this refers to a glucose moiety (e.g., a beta-D-glucosyl residue) being added to 5hmC to yield glucosyl 5-hydroxymethyl cytosine. The sugar blocking group can be any sugar or modified sugar that is a substrate of the glucosyltransferase enzyme and blocks the subsequent conversion of the 5hmC to 5caC and/or 5fC. The step of converting the 5mC in the DNA sample to 5caC and/or 5fC is then accomplished by the methods provided herein, such as by oxidation catalyzed by an enzyme, for example a TET enzyme.

Converting the 5caC and/or 5fC to DHU is accomplished by the methods provided herein, such by borane reduction.

In some embodiments, the enzyme catalyzing the addition of the sugar blocking group to the hydroxymethyl group of 5hmC and/or the enzyme converting the 5mC in the nucleic acid sample to 5-carboxylcytosine (5caC) and/or 5-formylcytosine (5fC) is inactivated by providing a protease, by a change in temperature, and/or by a change in pH. In some embodiments, the protease is selected from the group consisting of trypsin, endoproteinase AspN, endoproteinase GluC, proteinase K, furin, enterokinase, factor Xa, and subtilisin.

The method for identifying 5-methylcytosine (5mC) can be performed on an RNA sample to identify the location of, and provide a quantitative measure of, 5mC in a target RNA.

Methods for Identifying 5mC or 5hmC

In another aspect, the present disclosure provides a method for identifying 5mC or 5hmC in a target nucleic acid comprising the steps of:
    a. providing a nucleic acid sample comprising the target nucleic acid;

b. modifying the nucleic acid comprising the steps of:
       i. converting the 5mC and 5hmC in the nucleic acid sample to 5-carboxylcytosine (5caC) and/or 5fC; and
       ii. converting the 5caC and/or 5fC to DHU to provide a modified nucleic acid sample comprising a modified target nucleic acid; and
    c. detecting the sequence of the modified target nucleic acid comprising detecting the presence of DHU in the sequence, or converting the DHU to thymine (T) and detecting the presence of the thymine (T) in the sequence;
       wherein a cytosine (C) to DHU transition or a cytosine (C) to thymine (T) transition in the sequence of the modified target nucleic acid compared to the target nucleic acid provides the location of either a 5mC or 5hmC in the target nucleic acid;
    wherein steps i and ii are performed in a single tube and/or without a purification step between steps i and ii.

In embodiments of the method for identifying 5mC or 5hmC in the target nucleic acid, the method provides a quantitative measure for the frequency the of 5mC or 5hmC modifications at each location where the modifications were identified in the target nucleic acid. In embodiments, the percentages of a DHU or T at each transition location provide a quantitative level of 5mC or 5hmC at each location in the target nucleic acid.

This method for identifying 5mC or 5hmC provides the location of 5mC and 5hmC, but does not distinguish between the two cytosine modifications. Rather, both 5mC and 5hmC are converted to DHU. The presence of DHU can be detected directly, or the modified DNA can be replicated by known methods where the DHU is converted to T.

In one aspect, the step of converting the 5mC and 5hmC in the nucleic acid sample to 5-carboxylcytosine (5caC) and/or 5fC and the step of converting the 5caC and/or 5fC to DHU to provide a modified nucleic acid sample comprising a modified target nucleic acid are performed in a single tube or reaction vessel.

In one embodiment, the step of converting the 5mC and 5hmC in the nucleic acid sample to 5-carboxylcytosine (5caC) and/or 5fC is accomplished by the methods provided herein, such as by oxidation catalyzed by an enzyme, for example a TET enzyme.

In some embodiments, the enzyme catalyzing the conversion of the 5mC and 5hmC in the nucleic acid sample to 5-carboxylcytosine (5caC) and/or 5fC) is inactivated by providing a protease, by a change in temperature, and/or by a change in pH. In some embodiments, the protease is selected from the group consisting of trypsin, endoproteinase AspN, endoproteinase GluC, proteinase K, furin, enterokinase, factor Xa, and subtilisin.

The method for identifying 5mC or 5hmC can be performed on an RNA sample to identify the location of, and provide a quantitative measure of, 5mC or 5hmC in a target RNA.

Methods for Identifying 5mC and Identifying 5hmC

The present disclosure provides a method for identifying 5mC and identifying 5hmC in a target nucleic acid by (i) performing the method for identifying 5mC on a first nucleic acid sample described herein, and (ii) performing the method for identifying 5mC or 5hmC on a second nucleic acid sample described herein. The location of 5mC is provided by (i). By comparing the results of (i) and (ii), wherein a C to T (or C to DHU) transitions detected in (ii) but not in (i) provides the location of 5hmC in the target nucleic acid. In embodiments, the first and second nucleic acid samples are derived from the same nucleic acid sample.

For example, the first and second samples may be separate aliquots taken from a sample comprising DNA (or RNA) to be analyzed.

The above method identifies the locations and levels of 5hmC in the target nucleic acid through the comparison of 5mC locations and levels with the locations and levels of 5mC or 5hmC (together). In one aspect, the method comprises:

a. identifying 5mC in the target nucleic acid comprising the steps of:

i. providing a first nucleic acid sample comprising the target nucleic acid;

ii. modifying the nucleic acid in the first sample comprising the steps of:

1. adding a blocking group to the 5-hydroxymethyl-cytosine (5hmC) in the first nucleic acid sample;

2. converting the 5mC in the first nucleic acid sample to 5caC and/or 5fC; and 3. converting the 5caC and/or 5fC to DHU to provide a modified first DNA sample comprising a modified target nucleic acid, wherein steps 2 and 3 are performed in a single tube and/or without a purification step between steps 2 and 3, or wherein steps 1, 2, and 3 are performed in a single tube and/or without a purification step between steps 1, 2 and 3;

iii. detecting the sequence of the modified target nucleic acid comprising detecting the presence of DHU in the sequence, or converting the DHU to thymine (T) and detecting the presence of the thymine (T) in the sequence; wherein a cytosine (C) to DHU transition or a cytosine (C) to thymine (T) transition in the sequence of the modified target nucleic acid compared to the target nucleic acid provides the location of a 5mC in the target nucleic acid.

b. identifying 5mC or 5hmC in the target nucleic acid comprising the steps of:

i. providing a second nucleic acid sample comprising the target nucleic acid;

ii. modifying the nucleic acid in the second sample comprising the steps of:

1. converting the 5mC and 5hmC in the second nucleic acid sample to 5caC and/or 5fC; and 2. converting the 5caC and/or 5fC to DHU to provide a modified second nucleic acid sample comprising a modified target nucleic acid, wherein steps 1 and 2 are performed in a single tube and/or without a purification step between steps 1 and 2;

iii. detecting the sequence of the modified target nucleic acid from the second sample comprising detecting the presence of DHU in the sequence, or converting the DHU to thymine (T) and detecting the presence of the thymine (T) in the sequence; wherein a cytosine (C) to DHU transition or a cytosine (C) to thymine (T) transition in the sequence of the modified target nucleic acid compared to the target nucleic acid provides the location of either a 5mC or 5hmC in the target nucleic acid; and c. comparing the results of steps (a) and (b), wherein a C to DHU or C to T transition present in step (b) but not in step (a) provides the location of 5hmC in the target nucleic acid.

In some embodiments, the step of adding a blocking group to the 5-hydroxymethylcytosine (5hmC) in the first nucleic acid sample and the step of converting the 5mC in the first nucleic acid sample to 5caC and/or 5fC are performed in a single tube or reaction vessel without performing a purification between the steps.

In one embodiment, the blocking group added to the 5-hydroxymethylcytosine (5hmC) in the first nucleic acid sample is a sugar, including a modified sugar, for example glucose or 6-azide-glucose (6-azido-6-deoxy-D-glucose). The sugar blocking group is added to the hydroxymethyl group of 5hmC by contacting the nucleotide sample with uridine diphosphate (UDP)-sugar in the presence of an enzyme, for example a glucosyltransferase enzyme. The sugar blocking group can be any sugar or modified sugar that is a substrate of the glucosyltransferase enzyme and blocks the subsequent conversion of the 5hmC to 5caC and/or 5fC.

In embodiments, the glucosyltransferase is T4 bacteriophage $\beta$-glucosyltransferase ($\beta$GT), T4 bacteriophage $\alpha$-glucosyltransferase ($\alpha$GT), and derivatives and analogs thereof. $\beta$GT is an enzyme that catalyzes a chemical reaction in which a beta-D-glucosyl (glucose) residue is transferred from UDP-glucose to a 5-hydroxymethylcytosine residue in a nucleic acid.

In one embodiment, the conversion of the 5mC in the first nucleic acid sample to 5caC and/or 5fC and/or the conversion of the 5mC and 5hmC in the second nucleic acid sample to 5caC and/or 5fC is accomplished by the methods provided herein, such as by oxidation catalyzed by an enzyme, for example a TET enzyme.

Converting the 5caC and/or 5fC to DHU is accomplished by the methods provided herein, such by borane reduction.

In embodiments, the enzyme catalyzing the addition of the sugar blocking group to the hydroxymethyl group of 5hmC, the enzyme catalyzing the conversion of the 5mC in the first nucleic acid sample to 5caC and/or 5fC, and/or the enzyme catalzying the conversion of the 5mC and 5hmC in the second nucleic acid sample to 5caC and/or 5fC is inactivated by providing a protease, by a change in temperature, and/or by a change in pH. In some embodiments, the protease is selected from the group consisting of trypsin, endoproteinase AspN, endoproteinase GluC, proteinase K, furin, enterokinase, factor Xa, and subtilisin.

Methods for Identifying 5caC or 5fC

In one aspect, the invention provides a method for identifying 5caC or 5fC in a target DNA comprising the steps of:

a. providing a DNA sample comprising the target DNA;

b. converting the 5caC and/or 5fC to DHU to provide a modified DNA sample comprising a modified target DNA;

c. detecting the sequence of the modified target DNA; wherein a cytosine (C) to DHU transition or a cytosine (C) to thymine (T) transition in the sequence of the modified target DNA compared to the target DNA provides the location of either a 5caC or 5fC in the target DNA.

This method for identifying 5fC or 5caC provides the location of 5fC or 5caC, but does not distinguish between these two cytosine modifications. Rather, both 5fC and 5caC are converted to DHU, which is detected by the methods described herein. The methods for identifying 5fC or 5caC can be used to determine the levels of those modifications in samples also analyzed by the long-read methods for detecting 5mC and/or 5hmC described herein.

Blocking Detection of 5fC and/or 5caC

Because the 5mC and 5hmC (that is not blocked) are converted to 5fC and 5caC before conversion to DHU, any existing 5fC and 5caC in the DNA sample will be detected as 5mC and/or 5hmC. However, given the extremely low levels of 5fC and 5caC in genomic DNA under normal conditions, this will often be acceptable when analyzing methylation and hydroxymethylation in a DNA sample. The 5fC and 5caC signals can be eliminated by protecting the 5fC and 5caC from conversion to DHU by, for example, hydroxylamine conjugation and EDC coupling, respectively.

Adding a blocking group to the 5caC in the nucleic acid sample can be accomplished by (i) contacting the DNA sample with a coupling agent, for example a carboxylic acid derivatization reagent like carbodiimide derivatives such as 1-ethyl-3-(3-dimethylaminopropyl)carbodiimide (EDC) or N,N'-dicyclohexylcarbodiimide (DCC) and (ii) contacting the DNA sample with an amine, hydrazine or hydroxylamine compound. Thus, for example, 5caC can be blocked by treating the DNA sample with EDC and then benzylamine, ethylamine or other amine to form an amide that blocks 5caC from conversion to DHU by, e.g., pic-BH3. Methods for EDC-catalyzed 5caC coupling are described in WO2014165770, and are incorporated herein by reference.

Adding a blocking group to the 5fC in the nucleic acid sample can comprise contacting the DNA with an aldehyde reactive compound including, for example, hydroxylamine derivatives, hydrazine derivatives, and hyrazide derivatives. Hydroxylamine derivatives include ashydroxylamine; hydroxylamine hydrochloride; hydroxylammonium acid sulfate; hydroxylamine phosphate; O-methylhydroxylamine; O-hexylhydroxylamine; O-pentylhydroxylamine; O-benzylhydroxylamine; and particularly, O-ethylhydroxylamine (EtONH2), O-alkylated or O-arylated hydroxylamine, acid or salts thereof. Hydrazine derivatives include N-alkylhydrazine, N-arylhydrazine, N-benzylhydrazine, N,N-dialkylhydrazine, N,N-diarylhydrazine, N,N-dibenzylhydrazine, N,N-alkylbenzylhydrazine, N,N-arylbenzylhydrazine, and N,N-alkylarylhydrazine. Hydrazide derivatives include—toluenesulfonylhydrazide, N-acylhydrazide, N,N-alkylacylhydrazide, N,N-benzylacylhydrazide, N,N-arylacylhydrazide, N-sulfonylhydrazide, N,N-alkyl sulfonylhydrazide, N,N-benzyl sulfonylhydrazide, and N,N-aryl sulfonylhydrazide.

Determination of Whole Genome Methylomes

The method provided herein are useful for determine the whole genome methylome of an organism. As used herein, a methylome is a set of nucleic acid methylation modifications in an organism's genome or in a particular cell. In some embodiments, the method disclosed herein are useful for determining the whole genome methylome of a mammal (including but not limited to a human, a mouse, a rat, a rabbit, and a dog), a nematode, an insect, or a fish.

In one aspect, provided is a method for determining a whole genome methylome, the method comprising:

a. obtaining a nucleic acid sample that comprises a whole genomic DNA of a cell, wherein said whole genomic DNA comprises 5mC or 5hmC;

b. converting said whole genomic DNA into a modified whole genomic DNA; the converting step comprising:

i. converting the 5mC and 5hmC whole genomic DNA to 5-carboxylcytosine (5caC) and/or 5fC; and ii. converting the 5caC and/or 5fC to dihydrouracil (DHU) to provide a modified whole genomic DNA; wherein steps i and ii are performed in a single tube and/or without a purification step between steps i and ii; and c. identifying the location of the 5mC or the 5hmC in the modified whole genomic DNA; wherein said 5mC or 5hmC are identified at a single-nucleotide resolution; and wherein said modified whole genomic DNA is less degraded compared to a corresponding modified whole genomic DNA that has been contacted with bisulfite.

In one embodiment, the nucleic acid sample comprises less than or equal to about 100 ng of whole genomic DNA. In one embodiment, the whole genomic DNA comprises a plurality of unmodified cytostines which remain unmodified cytosines in the modified whole genomic DNA.

In embodiments, the step of identifying the location of 5mC or 5hmC in the modified whole genomic DNA comprises detecting a sequence of the modified whole genomic DNA comprising detecting the presence of DHU in the modified whole genomic DNA, or converting the DHU to thymine (T) and detecting the presence of the thymine (T) in the modified whole genomic DNA; and wherein a cytosine (C) to DHU transition or a cytosine (C) to thymine (T) transition in the modified whole genomic DNA compared to the whole genomic DNA provides the location of a 5mC or 5hmC in the whole genomic DNA.

In one embodiment, the step of converting the 5mC and 5hmC in the whole genomic DNA to 5-carboxylcytosine (5caC) and/or 5fC comprises contacting the whole genomic DNA with an enzyme, for example a TET enzyme described herein. In some embodiments, the TET enzyme is selected from the group consisting of human TET1, TET2, and TET3; murine Tet1, Tet2, and Tet3; *Naegleria* TET (NgTET); *Coprinopsis cinerea* (CcTET) and derivatives or analogues thereof.

In one embodiment, the step of converting the 5caC and/or 5fC to dihydrouracil (DHU) to provide a modified whole genomic DNA comprises contacting said whole genomic DNA with a reducing agent. In one embodiment, the reducing agent is a borane reducing agent, for example those described herein.

Long-Read Methods for Identifying Cytosine Modifications

The methods provided herein have certain steps performed in the same reaction tube and/or without a purification step in order to minimize fragmentation of long target nucleic acid sequences. As used herein, when two or three steps are performed without a purification step between the steps, this refers to the nucleic acid not being significantly purified (e.g., isolated from one or more components of the reaction mixture) between the particular steps. Methods for purifying nucleic acids that would not be employed between the specified steps are well known in the art (Sambrook et al., Molecular Cloning, A Laboratory Manual, 2nd ed. (Cold Spring Harbor Laboratory Press, Cold Spring Harbor, NY, 1989) at §§ 1.23-1.40, 2.73-2.80, 4.26-4.32 and 7.3-7.35) and include sequence-dependent or biospecific methods, including, but not limited to, affinity chromatography and hybridization to immobilized probes, as well as sequence-independent or physico-chemical methods, including, but not limited to, liquid-liquid extraction (including, but not limited to, extraction with phenol-chloroform), precipitation (including, but not limited to, precipitation with pure ethanol), extraction with filter paper, extraction with micelle-forming agents such as cetyl-trimethyl-ammonium-bromide, binding to immobilized, intercalating dyes (including, but not limited to acridine derivatives), adsorption to silica gels, glass particles, glass powder, silica particles, glass microfibers, and diatomaceous earth, and adsorption to magnetic glass particles (MGP), paramagnetic particles, or organo-silane particles under chaotropic conditions. Examples of the chaotropic material include guanidinium thiocyanate (GuSCN), guanidine hydrochloride (GuHCl), sodium iodide (NaI), potassium iodide (KI), sodium thiocyanate (NaSCN), urea, and combinations thereof. Another method for purifying nucleic acid is the so-called "batch-switch method" in which a nucleic acid-binding phase is contacted at a first pH with a nucleic acid-containing sample in which the nucleic acid-binding phase has a positive charge. To release or elute the nucleic acids, a second pH is set according to the charge-switch principle, which is higher than the pKs value of the nucleic acid-binding phase in order to invert or neutralize the positive charge, promoting detachment of the bound nucleic acids from the nucleic acid binding phase.

Nucleic Acid Sample/Target Nucleic Acid

The present invention provides methods for identifying the location of one or more of 5-methylcytosine, 5-hydroxymethylcytosine, 5-carboxyl cytosine and/or 5-formyl cytosine in a target nucleic acid quantitatively with base-resolution without affecting the unmodified cytosine. In embodiments, the target nucleic acid is DNA. In other embodiments, the target nucleic acid is RNA. Likewise the nucleic acid sample that comprises the target nucleic acid may be a DNA sample or an RNA sample.

The target nucleic acid may be any nucleic acid having cytosine modifications (i.e., 5mC or 5hmC, 5fC, and/or 5caC). The target nucleic acid can be a single nucleic acid molecule in the sample, or may be the entire population of nucleic acid molecules in a sample (or a subset thereof). The target nucleic acid can be the native nucleic acid from the source (e.g., cells, tissue samples, etc.) or can pre-converted into a high-throughput sequencing-ready form, for example by fragmentation, repair and ligation with adaptors for sequencing. Thus, target nucleic acids can comprise a plurality of nucleic acid sequences such that the methods described herein may be used to generate a library of target nucleic acid sequences that can be analyzed individually (e.g., by determining the sequence of individual targets) or in a group (e.g., by high-throughput or next generation sequencing methods).

A nucleic acid sample can be obtained from an organism from the Monera (bacteria), Protista, Fungi, Plantae, and Animalia Kingdoms. A nucleic acid sample can be obtained from a virus. Nucleic acid samples may be obtained from a from a patient or subject, from an environmental sample, or from an organism of interest. In embodiments, the nucleic acid sample is extracted or derived from a cell or collection of cells, a body fluid, a tissue sample, an organ, and an organelle.

RNA Sample/Target RNA

The present invention provides methods for identifying the location of 5-methylcytosine and/or 5-hydroxymethyl-cytosine in a target RNA quantitatively with base-resolution without affecting the unmodified cytosine. In embodiments, the RNA is one or more of mRNA (messenger RNA), tRNA (transfer RNA), rRNA (ribosomal RNA), snRNA (small nuclear RNA), miRNA (microRNA), lncRNA (long non-coding RNA) and eRNA (enhancer RNA). The target RNA can be a single RNA molecule in the sample, or may be the entire population of RNA molecules in a sample (or a subset thereof). Thus, target RNA can comprise a plurality of RNA sequences such that the methods described herein may be used to generate a library of target RNA sequences that can be analyzed individually (e.g., by determining the sequence of individual targets) or in a group (e.g., by high-throughput or next generation sequencing methods).

DNA Sample/Target DNA

The methods of the invention utilize mild enzymatic and chemical reactions that avoid the substantial degradation associated with methods like bisulfate sequencing. Thus, the methods of the present invention are useful in analysis of low-input samples, such as circulating cell-free DNA and in single-cell analysis.

In embodiments of the invention, the DNA sample comprises picogram quantities of DNA. In embodiments of the invention, the DNA sample comprises about 1 pg to about 900 pg DNA, about 1 pg to about 500 pg DNA, about 1 pg to about 100 pg DNA, about 1 pg to about 50 pg DNA, about 1 to about 10 pg, DNA, less than about 200 pg, less than about 100 pg DNA, less than about 50 pg DNA, less than about 20 pg DNA, and less than about 5 pg DNA. In other embodiments of the invention, the DNA sample comprises nanogram quantities of DNA. The sample DNA for use in the methods of the invention can be any quantity including, DNA from a single cell or bulk DNA samples. In embodiments, the methods of the present invention can be performed on a DNA sample comprising about 1 to about 500 ng of DNA, about 1 to about 200 ng of DNA, about 1 to about 100 ng of DNA, about 1 to about 50 ng of DNA, about 1 to about 10 ng of DNA, about 2 to about 5 ng of DNA, less than about 100 ng of DNA, less than about 50 ng of DNA less than 5 ng, and less than 2 ng of DNA. In embodiments of the invention the DNA sample comprises microgram quantities of DNA.

A DNA sample used in the methods described herein may be from any source including, for example a body fluid, tissue sample, organ, organelle, or single cells. In embodiments, the DNA sample is circulating cell-free DNA (cell-free DNA or cfDNA), which is DNA found in the blood and is not present within a cell. cfDNA can be isolated from blood or plasma using methods known in the art. Commercial kits are available for isolation of cfDNA including, for example, the Circulating Nucleic Acid Kit (Qiagen). The DNA sample may result from an enrichment step, including, but is not limited to antibody immunoprecipitation, chromatin immunoprecipitation, restriction enzyme digestion-based enrichment, hybridization-based enrichment, or chemical labeling-based enrichment.

The target DNA may be any DNA having cytosine modifications (i.e., 5mC, 5hmC, 5fC, and/or 5caC) including, but not limited to, DNA fragments or genomic DNA purified from tissues, organs, cells and organelles. The target DNA can be a single DNA molecule in the sample, or may be the entire population of DNA molecules in a sample (or a subset thereof). The target DNA can be the native DNA from the source or pre-converted into a high-throughput sequencing-ready form, for example by fragmentation, repair and ligation with adaptors for sequencing. Thus, target DNA can comprise a plurality of DNA sequences such that the methods described herein may be used to generate a library of target DNA sequences that can be analyzed individually (e.g., by determining the sequence of individual targets) or in a group (e.g., by high-throughput or next generation sequencing methods).

Converting 5mC and 5hmC to 5caC and/or 5fC

Embodiments of the present invention, such as the lrTAPS method described herein, include the step of converting the 5mC and 5hmC (or just the 5mC if the 5hmC is blocked) to 5caC and/or 5fC. In embodiments of the invention, this step comprises contacting the DNA or RNA sample with a ten eleven translocation (TET) enzyme. The TET enzymes are a family of enzymes that catalyze the transfer of an oxygen molecule to the N5 methyl group on 5mC resulting in the formation of 5-hydroxymethylcytosine (5hmC). TET further catalyzes the oxidation of 5hmC to 5fC and the oxidation of 5fC to form 5caC. TET enzymes useful in the methods of the invention include one or more of human TET1, TET2, and TET3; murine Tet1, Tet2, and Tet3; *Naegleria* TET (NgTET); *Coprinopsis cinerea* (CcTET) and derivatives or analogues thereof. In embodiments, the TET enzyme is NgTET. In other embodiments the TET enzyme is human TET1 (hTET1) and/or human TET2 (hTET2).

Converting 5caC and/or 5fC to DHU

Methods of the present invention include the step of converting the 5caC and/or 5fC in a nucleic acid sample to DHU. In embodiments, this step comprises contacting the DNA or RNA sample with a reducing agent including, for example, a borane reducing agent such as pyridine borane, 2-picoline borane (pic-BH$_3$), borane, sodium borohydride, sodium cyanoborohydride, and sodium triacetoxyborohydride. In a preferred embodiment, the reducing agent is pyridine borane and/or pic-BH$_3$. Technically, lrTAPS also detects the two minor DNA modifications, 5-formylcytosine (5fC) and 5caC. However, these modifications are typically present in small amounts in the mammalian genome (e.g., about less than 0.002% of total cytosine) and as such do not significantly influence the results obtained.

Amplifying the Copy Number of Modified Target Nucleic Acid

The methods of the invention may optionally include the step of amplifying (increasing) the copy number of the modified target nucleic acid by methods known in the art. When the modified target nucleic acid is DNA, the copy number can be increased by, for example, PCR, cloning, and primer extension. The copy number of individual target nucleic acids can be amplified by PCR using primers specific for a particular target nucleic acid sequence. Alternatively, a plurality of different modified target nucleic acid sequences can be amplified by cloning into a DNA vector by standard techniques. In embodiments of the invention, the copy number of a plurality of different modified target nucleic acid sequences is increased by PCR to generate a library for next generation sequencing where, e.g., double-stranded adapter DNA has been previously ligated to the sample DNA (or to the modified sample DNA) and PCR is performed using primers complimentary to the adapter DNA.

Detecting the Sequence of the Modified Target Nucleic Acid

In embodiments of the invention, the method comprises the step of detecting the sequence of the modified target nucleic acid. The modified target DNA or RNA contains DHU at positions where one or more of 5mC, 5hmC, 5fC, and 5caC were present in the unmodified target DNA or RNA. The DHU can be detected directly or the DHU can be detected as a C to T transition. DHU acts as a T in DNA replication and sequencing methods. Thus, the cytosine modifications can be detected by any direct or indirect method that identifies a C to T transition known in the art. Such methods include sequencing methods such as Sanger sequencing, microarray, and next generation sequencing methods, including, but not limited to single-molecule real-time (SMRT) sequencing, Ion semiconductor sequencing (Ion Torrent sequencing), sequencing by synthesis (Illumina), combinatorial probe anchor synthesis (cPAS-BGI/MGI), sequencing by ligation (SOLiD sequencing), and nanopore sequencing. The C to T transition can also be detected by restriction enzyme analysis where the C to T transition abolishes or introduces a restriction endonuclease recognition sequence. In particular, the method described herein are useful for detecting cytosine modifications using a long-read sequencing technology including PacBio Single-Molecule Real-Time (SMRT) sequencing and Oxford Nanopore sequencing.

Kits

The invention additionally provides kits for identification of 5mC and/or 5hmC in a target nucleic acid. Such kits comprise reagents for identification of 5mC and/or 5hmC by the methods described herein. In embodiments, the kit comprises a TET enzyme, a borane reducing agent and instructions for performing the method. In further embodiments, the TET enzyme is TET1 or TET2 and the borane reducing agent is selected from one or more of the group consisting of pyridine borane, 2-picoline borane (pic-BH$_3$), borane, sodium borohydride, sodium cyanoborohydride, and sodium triacetoxyborohydride. In a further embodiment, the TET1 enzyme is NgTet1 or murine Tet1 and the borane reducing agent is pyridine borane and/or pic-BH$_3$. In a further embodiment, the TET enzyme is hTET2 and the borane reducing agent is pyridine borane and/or pic-BH$_3$.

In embodiments, the kit further comprises a 5hmC blocking group and a glucosyltransferase enzyme. In further embodiments, the 5hmC blocking group is uridine diphosphate (UDP)-sugar where the sugar is glucose or a glucose derivative, and the glucosyltransferase enzyme is T4 bacteriophage β-glucosyltransferase (βGT), T4 bacteriophage α-glucosyltransferase (αGT), and derivatives and analogs thereof.

In embodiments, the kit comprises reagents for isolating DNA or RNA. In embodiments the kit comprises reagents for isolating low-input DNA from a sample, for example cfDNA from blood, plasma, or serum.

EXAMPLES

Methods

Preparation of Model DNA and Spike-In Control 4 kb model DNA was prepared by PCR amplification of pNIC28-Bsa4 plasmid (Addgene) and the reaction contained 1 ng DNA template, 0.5 μM primers and 1× Phusion High-Fidelity PCR Master Mix with HF Buffer (Thermo Scientific). Primers sequences were as follows: forward primer 5'-ACTGGAACAACACTCAACCCTA-3' (SEQ ID NO:1) and reverse primer 5'-AGGGTGGTGAATGT-GAAACC-3' (SEQ ID NO:2). PCR conditions were as follows: Initial Denaturation (98° C. for 30 s), 25 cycles of (98° C. for 10 s, 62° C. for 15 s, 72° C. for 63 s), final extension (72° C. for 10 min). The PCR product was purified by Zymo-IC column (Zymo Research) with Buffer PB (Qiagen) and the concentration was measured with Qubit dsDNA HS Assay Kit (ThermoFisher) and purity checked by 1% agarose gel electrophoresis. The purified amplicon (1 μg DNA) was methylated by HpaII Methyltransferase (NEB) for 2 h at 37° C. in a 50 μL solution comprising 5 μL 10× CutSmart buffer, 1 μL SAM (32 mM), and 2.5 μL HpaII methyltransferase (4 U/μL). After 2 h, 1.25 of HpaII methyltransferase and 1 μL of SAM were added to the reaction and incubated at 37° C. for another 2 h. The reaction was purified with 1× Ampure XP beads (Beckman Coulter) according to the manufacturer's protocol. DNA methylation was validated by HpaII digestion and 50 ng of methylated and unmethylated DNA digested in a 10 μL reaction with 2 U of HpaII restriction endonuclease (NEB) in 1× CutSmart buffer (NEB) for 1 h at 37° C. Unmethylated lambda DNA (Promega) was methylated with the same protocol above for CmCGG methylation.

Cell Culture and Isolation of Genomic DNA

E14 mESCs were cultured on gelatin-coated plates in DMEM (Invitrogen) supplemented with 15% FBS (Gibco), 2 mM 1-glutamine (Gibco), 1% nonessential amino acids (Gibco), 1% penicillin/streptavidin (Gibco), 0.1 mM β-mercaptoethanol (Sigma), 1,000 units ml-1 leukemia inhibitory factor (Millipore), 1 μM PD0325901 (Stemgent) and 3 μM CHIR99021 (Stemgent). Huh-1 and HepG2-NTCP cells were maintained in Dulbecco's Modified Eagles Medium (DMEM) supplemented with 10% FBS, 2 mM L-glutamine, 1 mM Sodium Pyruvate, 50 U/mL penicillin/streptomycin and non-essential amino acids (ThermoFisher Scientific). HBV ayw stocks were purified from HepAD38 producer cells as described in Ko et al., J Hepatol. 2018; 69(6):1231-41. HepG2-NTCP cells were treated with 2.5% dimethyl sulphoxide (DMSO) for 3 days and inoculated with HBV at a multiplicity of infection of 200 in the presence of 4% polyethylene glycol 8000. After 18-20 h the inoculation was removed by washing with PBS and cells cultured in the presence of 2.5% DMSO. Cultures were maintained at 37° C. and 5% $CO_2$. For isolation of genomic DNA, cells were harvested by centrifugation for 5 min at 1,000 g and room temperature. DNA was extracted with Quick-DNA Plus kit (Zymo Research) according to the manufacturer's protocol.

Expression and Purification of hTet2

Protein was expressed in *E. coli* BL21 (DE3) from pET28a plasmid encoding engineered hTet2 protein (1129-1936-Δ(1481-1843), deletion replaced by 15 amino acids GS-linker) with 6×His-Flag-SUMO N-terminal tag (Hu L et al. Nature. 2015; 527(7576):118-22.). Overnight small-scale bacteria culture were grown in LB medium supplemented with 50 µg/mL kanamycin at 37° C. and 200 rpm until OD600 was between 0.75-0.9. Then cultures were cooled down to room temperature and target protein expression was induced with 0.2 mM isopropyl-β-d-1-thiogalactopyranoside (IPTG). Cells were maintained for additional 18 hours at 18° C. and 180 rpm. Subsequently, cells were harvested and re-suspended in the lysis buffer containing 20 mM HEPES pH=7.4, 500 mM NaCl, 20 mM imidazole, 0.5 mM TCEP, 1× cOMPLETE protease inhibitors cocktail. Cells were broken by sonication and lysate was clarified by centrifugation for 1 hour at 30000×g and 4° C. Collected supernatant was loaded on Ni-NTA resins and hTet2 protein was eluted with buffer containing 50 mM HEPES pH=7.4, 500 mM NaCl, 250 mM imidazole, 0.5 mM TCEP. Collected fractions were then purified on HiLoad 16/60 Sdx 75 (50 mM HEPES pH=7.5, 500 mM NaCl, 0.5 mM TCEP). Fractions containing hTet2 were then collected, concentrated and buffer exchanged to the final buffer containing 50 mM HEPES pH=7.5, 200 mM NaCl, 0.5 mM TCEP. Pure protein was mixed with glycerol (30% v/v) and aliquots were stored at −80° C.

Long-Read TAPS

The reaction was performed in a total volume of 20 µL in a 1.5 mL DNA LoBind Tubes (Eppendorf) using up to 100 ng (final concentration) of purified DNA, 6 µL hTet2 buffer, 1.4 µL 1.5 mM Fe, and 4 µM (final concentration) hTet2. hTet2 buffer comprises 167 mM HEPES pH=7.0, 333 mM NaCl, 3.3 mM α-ketoglutaric acid, 6.67 mM L-ascorbic acid, 4 mM ATP, 8.33 mM DTT. 1.5 mM Fe. Optionally, 0.5%-1% methylated lambda DNA was added to the purified DNA sample as spike-in control for conversion test.

The reaction was incubated at 30° C. for 80 min. 1 µL of Proteinase K (NEB, 0.8 µL) was added to the oxidation reaction and incubated for 1 h at 50° C. 6 µL of 3 M sodium acetate buffer solution (pH 4.3) and 3 µL of pyridine borane (Alfa Aesar, —10 M) were added to the 21 µL DNA sample (final 30 µL reaction contains 600 mM NaAc and 1 M pyridine borane). The solution was incubated at 37° C. and 850 rpm in a ThermoMixer (Eppendorf) for 16 h. The reaction was purified on Zymo-IC column (Zymo Research) with Oligo binding buffer (Zymo Research) according to the manufacturer's protocol and eluted in 20 µL of water. Optionally, the concentration of converted DNA was determined with Qubit dsDNA HS Assay Kit and recovery was calculated. A typical recovery yield was 40% to 80%. The converted DNA was amplified with LongAmp Hot Start Taq 2× Master Mix (NEB) and primers for target regions (see Table 1) using following PCR program: Initial Denaturation (94° C. for 30 s), 25 cycles of (94° C. for 10 s, annealing temperature, see Table 1, for 15 s, 65° C. for 50 s per kb), final extension (65° C. for 10 min). The PCR product was purified with Ampure XP beads according to the manufacturer's protocol. The DNA concentration was measured with Qubit™ dsDNA HS Assay Kit and the quality and purity was confirmed on 1% agarose gel.

TABLE 1

Primer used for lrTAPS

| Template | Primer | Sequence (5' to 3') | SEQ ID NO: | Note | Ta |
|---|---|---|---|---|---|
| 4 kb model DNA | 4 kb-F | CATCGAGCATCAAATGA AACTGC | 3 | Nano-TAPS: 4 kb-F and 4 kb-R, amplicon size 4015 bp | 60° C. |
| | 4 kb-R | ACGTTATACGATGTCGC AGAGT | 4 | SMRT-TAPS: 4 kb-F-BstAPI (to | |
| | 4 kb-F-BstAPI | ATCAGGTGGCACACTCT ATCTCGGAAGCAGACTC TGCCATCGAGCATCAAA TGAAACTGC | 5 | introduce BstAPI restriction enzyme site for stick-end ligation) and 4 kb-R | |
| Lambda DNA | Lambda-F1 | CTTCGGCCTGTGTCAGTT CT | 6 | Combinations of primers for | 60° C. |
| | Lambda-F2 | AACGTCTCTTCAGGCCA CTG | 7 | amplicons with different length: | |
| | Lambda-F3 | ATCGCACCATCAGCCAG AAA | 8 | F3R1-2932 bp; F5R3-3333 bp; | |
| | Lambda-F4 | GGTGTGGCAAAGCTTGA AGG | 9 | F4R3-3597 bp; F2R1-5005 bp; | |
| | Lambda-F5 | CTTACCCAACCCACCTG GTC | 10 | F3R2-5646 bp; F2R2-7719 bp; | |
| | Lambda-R1 | CGGATATCCCACAGGTG AGC | 11 | F3R3-8422 bp; F1R1-10155 bp; | |
| | Lambda-R2 | GCTCAGTTTGGGTTGTGC TG | 12 | F2R3-10495 bp | |
| | Lambda-R3 | CCATGCGCTTGCTCTTCA TC | 13 | | |

TABLE 1-continued

Primer used for lrTAPS

| Template | Primer | Sequence (5' to 3') | SEQ ID NO: | Note | Ta |
|---|---|---|---|---|---|
| mESC gDNA | Chr11-F | ACGCCCTTGGAGGGCAT A | 14 | Expected amplicon size 4053 bp | 60° C. |
| | Chr11-R | AGGGCATGGGTGGAGAC TAT | 15 | | |
| | Chr13-F | TTAGCTGCACCTTTGTGC TT | 16 | Expected amplicon size 4407 bp | 60° C. |
| | Chr13-R | TTGCACCCTGTCTGCAAT CT | 17 | | |
| HBV cccDNA | ApaLI-F | CACGTCGCATGGAGACC AC | 18 | Expected amplicon size ~3.2 kb | 60° C. |
| | ApaLI-R | CCGGCAGATGAGAAGGa ACAG | 19 | | |
| Huh-1 DNA HBV | HepB8F | CTTATAGACCACCAAAT GCCCCTA | 20 | Expected amplicon size ~2.1 kb | 58° C. |
| | HepB22R | CAAAACAAGCGGCTAGG AGTTC | 21 | | |

Illumina TAPS

Genomic DNA was fragmented with Covaris M220 instrument to desired length (e.g. —200 bp) in EB buffer and size-select with AMPure XP beads (e.g. 0.55×-1× for 200 bp-400 bp). Necessary control spike-ins were added before or after the fragmentation, depending on the length.

100 ng of fragmented and size selected DNA from above was used for end-repair and A-tailing reaction with KAPA Hyper kit. For the ligation step, use following pre-annealed adapters instead of the standard KAPA index adapters: 5'-ACACTCTTTCCCTACACGACGCTCTTCCGATCT-3' (SEQ ID NO:22) (IDT, HPLC purified) and 5'-/5Phos/ GATCGGAAGAGCACACGTCT-3' (SEQ ID NO:23) (IDT, HPLC purified). Ligated DNA was purified with 0.88× AMPure XP beads and eluted in 20 μL of nuclease-free water. The hTet2 oxidation reaction was performed in a total volume of 50 μL using 20 μL of purified DNA, 15 μL hTet2 buffer, 3.3 μL 1.5 mM Fe, and 4 μM (final concentration) hTet2. hTet2 buffer comprises 167 mM HEPES pH=7.0, 333 mM NaCl, 3.3 mM α-ketoglutaric acid, 6.67 mM L-ascorbic acid, 4 mM ATP, 8.33 mM DTT. 1.5 mM Fe.

The reaction was incubated at 30° C. for 80 min. 2 μL of Proteinase K (NEB, P8107S, 0.8 U/μL) was added to the oxidation reaction and incubate for 1 h at 50° C. The oxidation reaction was purified with 1.8×AMPure XP beads and eluted in 20 μL of nuclease-free water. Steps were repeated to achieve more complete oxidation. Double-oxidized DNA was eluted in 35 μL of nuclease-free water.

10 μL of 3 M NaAc pH=4.3 and 5 μL of pyridine borane were added to the 35 DNA sample. The sample was incubated at 37° C. and 850 rpm in a ThermoMixer (Eppendorf) for 16 h. The reaction was purified on Zymo-IC column (Zymo Research) with Oligo binding buffer (Zymo Research). The samples was eluted in 15 μL of water and amplified the converted DNA in 50 μL PCR reaction with KAPA HiFi HotStart Uracil+ReadyMix (KAPA) and indexed primers in NEBNext Multiplex Oligos for Illumina kit (NEB). PCR conditions were as follows: Initial Denaturation (98° C. for 45 s), 4 cycles of (98° C. for 15 s, 60° C. for 30 s, 72° C. for 30 s), final extension (72° C. for 1 min). The PCR product was purified with 1× Ampure XP beads. The concentration was measured with Qubit dsDNA HS Assay Kit (Invitrogen) and the library checked on a 2% agarose gel.

Restriction Enzyme Digestion Assay

After PCR amplification, 50 ng of lrTAPS product was incubated with 4 units of HpaII restriction enzyme (New England Biolabs) in 1×CutSmart buffer (New England Biolabs) for 30 min at 37° C. and then visualized by 2% agarose gel electrophoresis. For successful lrTAPS conversion, the restriction site (CCGG) is lost due to the C-to-T transition and so the amplicon would remain intact. Genomic DNA samples were spiked-in with 0.5% of methylated 4 kb model DNA and lrTAPS conversion was validated by HpaII digestion assay on the model DNA.

Bisulfite Sequencing 50 ng of methylated 4 kb model DNA or lambda-DNA were fragmented to by Covaris M220 instrument and size-selected to 200-400 bp using Ampure XP beads. End-repair and A-tailing reaction and ligation of methylated adapter (NextFlex) were prepared with KAPA HyperPlus kit (Kapa Biosystems) according to manufacturer's protocol. Subsequently, DNA underwent bisulfite conversion with EpiTect Bisulfite Kit (Qiagen) according to manufacturer's protocol. The final library was amplified with KAPA Hifi Uracil Plus Polymerase (Kapa Biosystems) for 6 cycles and cleaned up on 1× Ampure XP beads. The BS-seq library was paired-end 80 bp sequenced on a NextSeq 500 sequencer (Illumina).

Nanopore Sequencing 4 kb model DNA samples were sequenced on one MinION R9.4.1 RevD flow cell while mESCs and HBV samples were sequenced on one Flongle R9.4.1 flow cell. One μg and 250 ng of each PCR product was used in the standard Native Barcoding genomic DNA (with EXP-NBD104, EXP-NBD114 and SQK-LSK109) protocol for the MinION and Flongle run, respectively. Reads were base called with guppy-2.3.5 flip flop model and demultiplexed with guppy_barcoder (v 2.3.5). Adapters in reads were trimmed with Porechop (v 0.2.3).

SMRT Sequencing 4 kb model DNA lrTAPS product was double-digested by BstAPI restriction enzyme (NEB) then ligated with modified SMRTbell adaptor (IDT, sequence 5' to 3'/5Phos/GT-AGTCTCGCACAGATATCTCTCTCTTTTCCTCCTCCT-CCGT- TGTTGTTGTT GAGAGAGATATCTGTGCGA-GACTACAGT (SEQ ID NO:24), extra AGT overhang was added for the stick-end ligation) by Instant Sticky-end Ligase Master Mix (NEB). SMRTbell Template Prep Kit 1.0

(Pacbio) and standard 16-base barcode SMRTbell adaptors (IDT) were used for library preparation of lambda DNA, mESCs and HBV samples. SMRTbell libraries were pooled in equimolar amounts for a total of 300 ng. For sequencing, the pooled SMRTbell library was bound with Sequel II Binding Kit 2.0, sequenced with Sequel II Sequencing Plate 2.0 using a 30-hour movie with 1 hr pre-extension time. Data were demultiplexed and CCS reads computed using the SMRT Analysis package (Pacific Biosciences) with minimum 3 passes and minimum predicted accuracy=Q20.

Native Methylation Calling for Nanopore Reads

CmCGG methylated 4 kb model DNA was used to evaluate the accuracy of native methylation calling algorithm for Nanopore sequencing. For Nanopolish (0.9.2) (Simpson et al., Nat Methods. 2017; 14 (4): 407-10), nanopolish index was used to build an index mapping from basecalled reads and minimap2 2.16-r922 was used to align reads to reference with –x map-ont option. Methylated CpG was then detected with nanopolish call-methylation module, and calculate_methylation_frequency.py was used to calculate methylation. For Tombo (1.5) (Stoiber et al., available on the world wide web at doi.org/10.1101/094672 (2017). Accessed 3 Dec. 2019), tombo preprocess annotate_raw_with fastqs was used to annotate read files with baseballs in FASTQ format. Tombo resquiggle was used to align raw signal to reference and tombo detect modifications alterna- 3094-100) with –x map-ont option. For 4kb model DNA, from 2,627 to 6,911 of pNIC28-Bsa4 sequence was used as reference. It's worth noting that a 3 bp TAT deletion (position: 1,996-1,998) was detected in BS-seq, Nano-TAPS and SMRT-TAPS and thus removed from the reference. For E14 mESCs, mm9 gnome was used as reference. For lambda DNA, the reference can be found under accession J02459. For HBV, the reference of HBV ayw strain can be found under accession number KX470733. The reads were filtered by length (as summarized in Table 2), and methylated CpG was detected using a custom R script (mCG_lrtaps.r). Theoretically, the methylated CG was converted to TG or CA after TAPS, while un-methylated CG remained to be CG. The CG methylation ratio was thus calculated as the (TG+CA)/(TG+CA+CG). In HBV genome specifically, (TG+CA+CG)/NN>0.8 and non-TAPS control was used to distinguish methylated CpG from single nucleotide polymorphisms (SNP). To evaluate the performance of lrTAPS in 4kb as compare to BS-seq, we performed Receiver operating characteristic (ROC) analysis. CpG sites with methylation level higher than 3% in bisulfite sequencing was designated as methylated, while methylation level lower than this cut-off was designated as un-methylated. ROC was used to evaluate the performance of different method with plotROC package (available on the world wide web at cran.r-project.org/web/packages/plotROC), and calc_auc was used to compute the area under receiver (AUC).

TABLE 2

Sequencing and mapping statistics for long-read TAPS.

| Sample | # Raw reads | # Raw bases | Average length | # Mapped reads | length filter criteria(bp) | # reads after filtering |
|---|---|---|---|---|---|---|
| nanopore_4kb.ccgg_meth.noTAPS | 26,845 | 111,775,211 | 4,164 | 26,842 | 3,500 | 25,377 |
| nanopore_4kb.ccgg_meth.TAPS | 33,473 | 96,610,038 | 2,886 | 33,459 | 3,500 | 20,970 |
| pacbio_4kb.ccgg_meth.TAPS | 14,614 | 58,127,652 | 3,978 | 14,608 | 3,500 | 6,003 |
| nanopore_lambda.ccgg_meth.TAPS | 22,043 | 116,830,121 | 5,300 | 21,908 | 8,000 | 7,331 |
| pacbio_lambda.ccgg_meth.TAPS | 244,319 | 2,032,755,069 | 8,320 | 244,317 | 8,000 | 176,045 |
| nanopore_mESC_chr11.32183629_32187681.TAPS | 33,213 | 128,786,174 | 3,878 | 33,128 | 3,000 | 31,036 |
| nanopore_mESC_chr13.101123190_101127596.TAPS | 18,449 | 74,283,198 | 4,026 | 18,400 | 3,000 | 16,355 |
| pacbio_mESC_chr11.32183629_32187681.TAPS | 240,368 | 979,074,104 | 4,073 | 240,363 | 3,000 | 238,840 |
| pacbio_mESC_chr13.101123190_101127596.TAPS | 102,399 | 448,827,358 | 4,383 | 102,396 | 3,000 | 100,453 |
| nanopore_hbv_cccDNA.TAPS | 23,472 | 70,973,805 | 3,024 | 23,339 | 3,000 | 21,479 |
| pacbio_hbv_cccDNA.TAPS | 80,436 | 259,298,934 | 3,224 | 80,418 | 3,000 | 79,074 |
| nanopore_hbv_huh1.TAPS | 28,688 | 57,271,499 | 1,996 | 26,848 | 2,000 | 23,127 |
| pacbio_hbv_huh1.TAPS | 34,973 | 78,186,883 | 2,236 | 34,895 | 2,000 | 34,756 | tive_model was used to detect methylated CpG with—alternate-bases CpG—dna—multiprocess-region-size 1000—processes 2 options.

WGBS and lrTAPS Data Processing

For WGBS in 4 kb model DNA or lambda-DNA, fastp (Chen et al, Bioinformatics. 2018; 34(17):i884-i90.) was used to preprocess the FASTQ files and bismark (v0.22.0) (Krueger et al, Bioinformatics. 2011; 27(11):1571-2) was used to map clean reads to reference. MarkDuplicates was used to remove PCR duplicates and bismark_methylation_extractor was used to extract methylation ratio. For lrTAPS in E14 mESCs, published data GSE112520 was processed as previously described (Liu Y, Siejka-Zielinska et al., Nat Biotechnol. 2019; 37(4):424-9). Integrative Genomics Viewer (IGV) (Robinson et al., Nat Biotechnol. 2011; 29(1): 24-6) was used to visualize individual long-read from Nano-TAPS and SMRT-TAPS and coverage/methylation in E14 mESCs and lambda-DNA.

Methylation Calling for lrTAPS

Long reads were mapped to reference genome using minimap2 (2.16-r922) (Li, Bioinformatics. 2018; 34 (18):

CGI Detection in HBV

The CpG Islands in HBV genome were predicted with urogene.org/cgi-bin/methprimer/methprimer.cgi.

Example 1: lrTAPS can be Used to Detect 5mC with High Sensitivity and Specificity Discussed below is the development of a convenient method (termed long-read TAPS, lrTAPS) for the detection of DNA and RNA methylation pattern that minimizes the loss of long DNA molecules, allows for low DNA input, and is compatible with both nanopore as well as SMRT sequencing. This method utilizes mild reactions based on ten-eleven translocation (TET) enzyme oxidation of 5mC to 5-carboxylcytosine (5caC) and subsequent pyridine borane reduction of 5caC to dihydrouracil (DHU), wherein the TET oxidation and pyridine borane reduction are performed in the same tube (see FIG. 1a). During PCR amplification, DHU is recognized as thymine, resulting in a 5mC-to-T transition.

To demonstrate the ability of lrTAPS to detect 5mC with high sensitivity and specificity, a 4 kb model DNA treated with HpaII methyltransferase was used. This enzyme methylates the internal cytosine residue in C-C-G-G sequences to C-5mC-G-G, while generating low-level off-target methylation in related sequences. The recombinant, *E. coli*-expressed human TET2 (hTet2) was used rather than mammalian, cell-expressed mouse Tet1 (mTet1), hTet2 can be produced in high yield and at low cost while retaining comparable activity (see Table 3).

TABLE 3

Comparison of hTet2 and mTet1CD activity by Illumina-TAPS.
An unmodified 2 kb amplicon was used to calculate conversion
rate of unmodified C (false-positive rate). A synthetic
oligonucleotide containing both a methylated and hydroxymethylated
C surrounded by any other base (N5mCNN and N5hmCNN, respectively)
was used to compare the conversion rate on 5mC and 5hmC
in different sequence contexts.

| TAPS conversion rate | hTet2 | mTet1CD |
|---|---|---|
| mCpG | 97.3% | 97.3% |
| mCpH | 74.0% | 85.9% |
| hmCpG | 88.2% | 89.1% |
| hmCpH | 66.2% | 80.5% |
| Unmodified C | 0.19% | 0.23% |

The model DNA was treated using the lrTAPS method as described in the Methods section, followed by long-range PCR amplification. The resulting amplicon was sequenced on both Oxford Nanopore and SMRT sequencing platforms (termed Nano-TAPS and SMRT-TAPS respectively), with methylation sites identified by CG-to-TG/CA substitutions compared to the reference sequence. For comparison, the methylation status of the 4 kb model DNA was determined by BS-seq using Illumina sequencing (FIG. 1B).

Both Nano-TAPS and SMRT-TAPS successfully detected all of the methylated CCGG sites and most of the off-target sites showing a high agreement with BS-Seq data (Pearson correlation coefficient 0.992 and 0.999, respectively). SMRT-TAPS detected 5mC with only 3 passes in the single-molecular circular consensus sequence (CCS) mode and achieved higher accuracy than Nano-TAPS, consistent with the recent improvement in the accuracy of SMRT sequencing (FIG. 1B and FIG. 2A). Further, the non-amplified TAPS-treated DNA, which contains DHU, was also subjected to SMRT sequencing. It was found that the non-amplified TAPS-treated DNA stalls the polymerase used in the system (data not shown), suggesting DHU is incompatible with SMRT sequencing. When the native model DNA (i.e., without lrTAPS treatment) was sequenced by Nanopore sequencing and methylation sites were called using Nanopolish or Tombo software, a reduced agreement with BS-seq data was observed (Pearson correlation coefficient 0.65 and 0.808, respectively, FIG. 1B and FIG. 2A). Receiver operating characteristic (ROC) analysis confirmed Nano-TAPS and SMRT-TAPS outperformed native Nanopore methylation sequencing with sensitivity and specificity comparable to Illumina sequencing (FIG. 2B).

Example 2: lrTAPS can be Used to Detect DNA Methylation in Long DNA Molecules To further confirm that lrTAPS is useful for the methylation analysis of long DNA molecules, HpaII methylated phage lambda DNA (48 kb) was used. After lrTAPS conversion, the methylated DNA was PCR amplified to generate amplicons ranging from 3-10 kb (see Table 2). Complete lrTAPS conversion was confirmed by HpaII digestion (FIG.

3) and the longest 10 kb amplicon was sequenced by Oxford Nanopore and SMRT sequencing.

Figure 4:
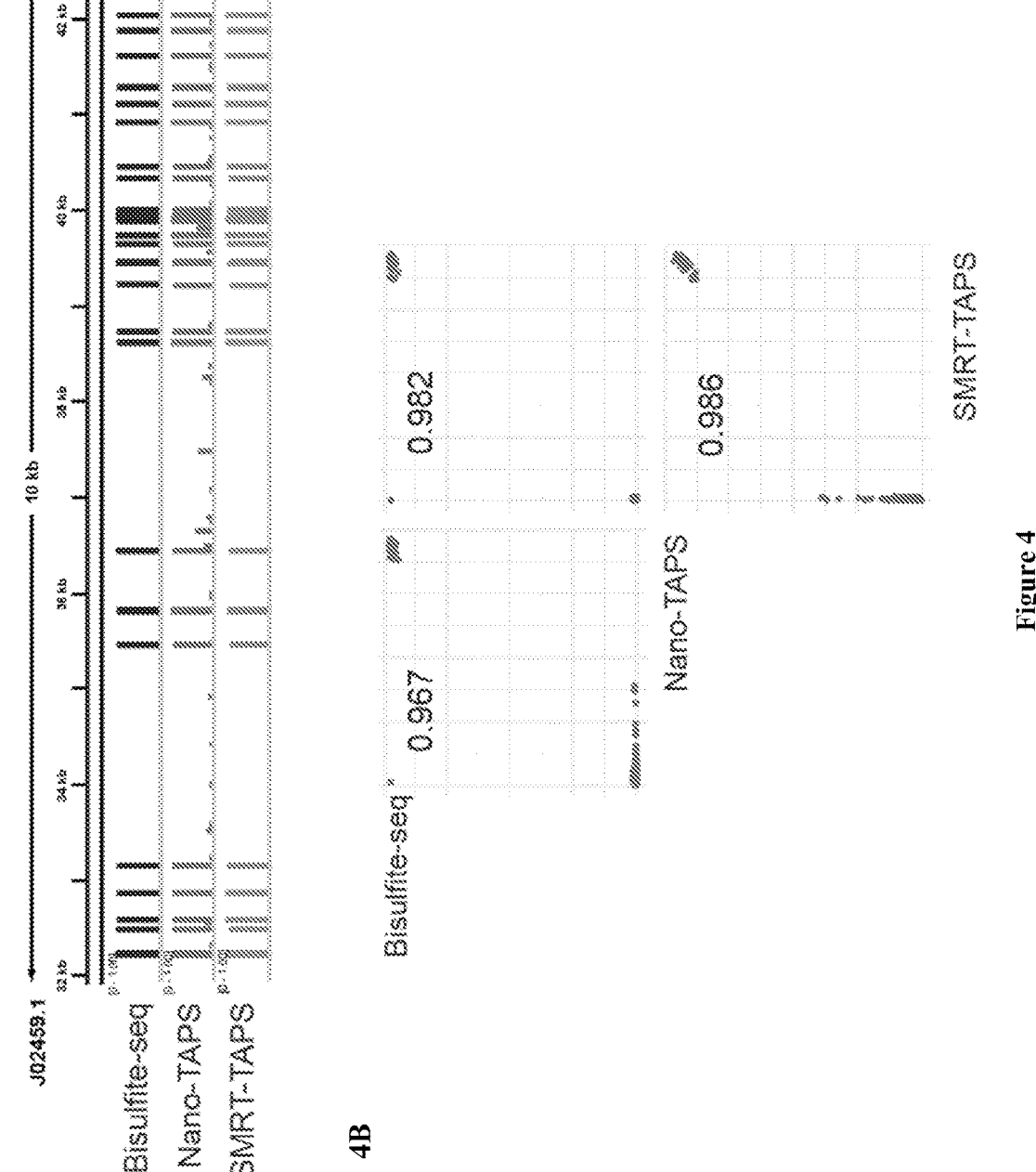
FIGS. 4A and 4B illustrate that lrTAPS allows accurate detection of DNA methylation in regions up to 10 kb. 4A. Integrative Genomics Viewer (IGV) snapshot depicting methylation in the 10 kb amplicon from lambda model DNA detected by BS-seq, Nano-TAPS and SMRT-TAPS. 4B. Scatter plot showing all pairwise correlation among the methylation level detected by BS-seq, Nano-TAPS and SMRT-TAPS within all the CpG sites in the amplified region of the lambda, with correlation coefficient showing on top of each plot.

For both platforms, excellent agreement with BS-seq data in detecting DNA methylation was observed (Pearson correlation coefficient 0.967 and 0.982, respectively (FIG. 4).

Example 4: lrTAPS can be Used to Provide Accurate DNA Methylation Maps of Previously Inaccessible Non-Unique Genomic Regions To demonstrate that lrTAPS can be used to characterize difficult-to-map DNA and close gaps in human genome assemblies, the method was applied to 50 ng of E14 mouse embryonic stem cell (mESC) genomic DNA. A 4 kb region that spans a 500 bp gap previously identified on chromosome 11 was amplified.

Figure 5:
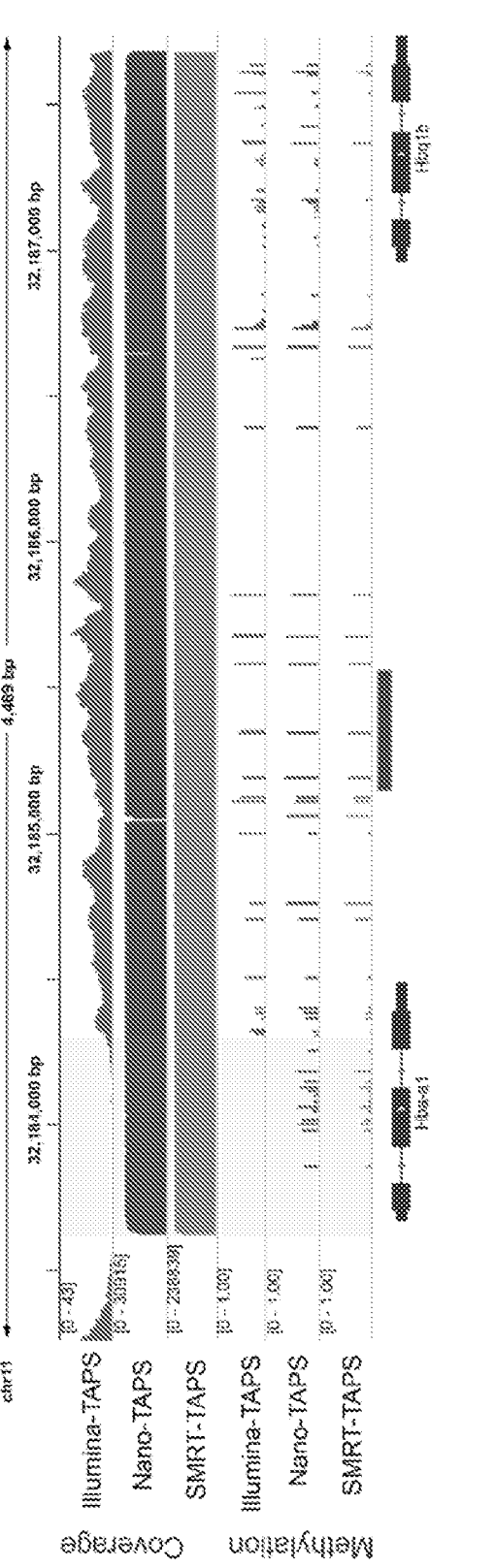
FIG. 5 illustrates the application of lrTAPS to a previously unmapped region in mESCs and integrated HBV DNA in Huh-1 cells. Genome browser view of the methylation and coverage detected by Illumina-TAPS, Nano-TAPS and SMRT-TAPS in Hba-a1 locus. The shaded area shows the gap which cannot be mapped with Illumina short-read sequencing.
Figure 7:
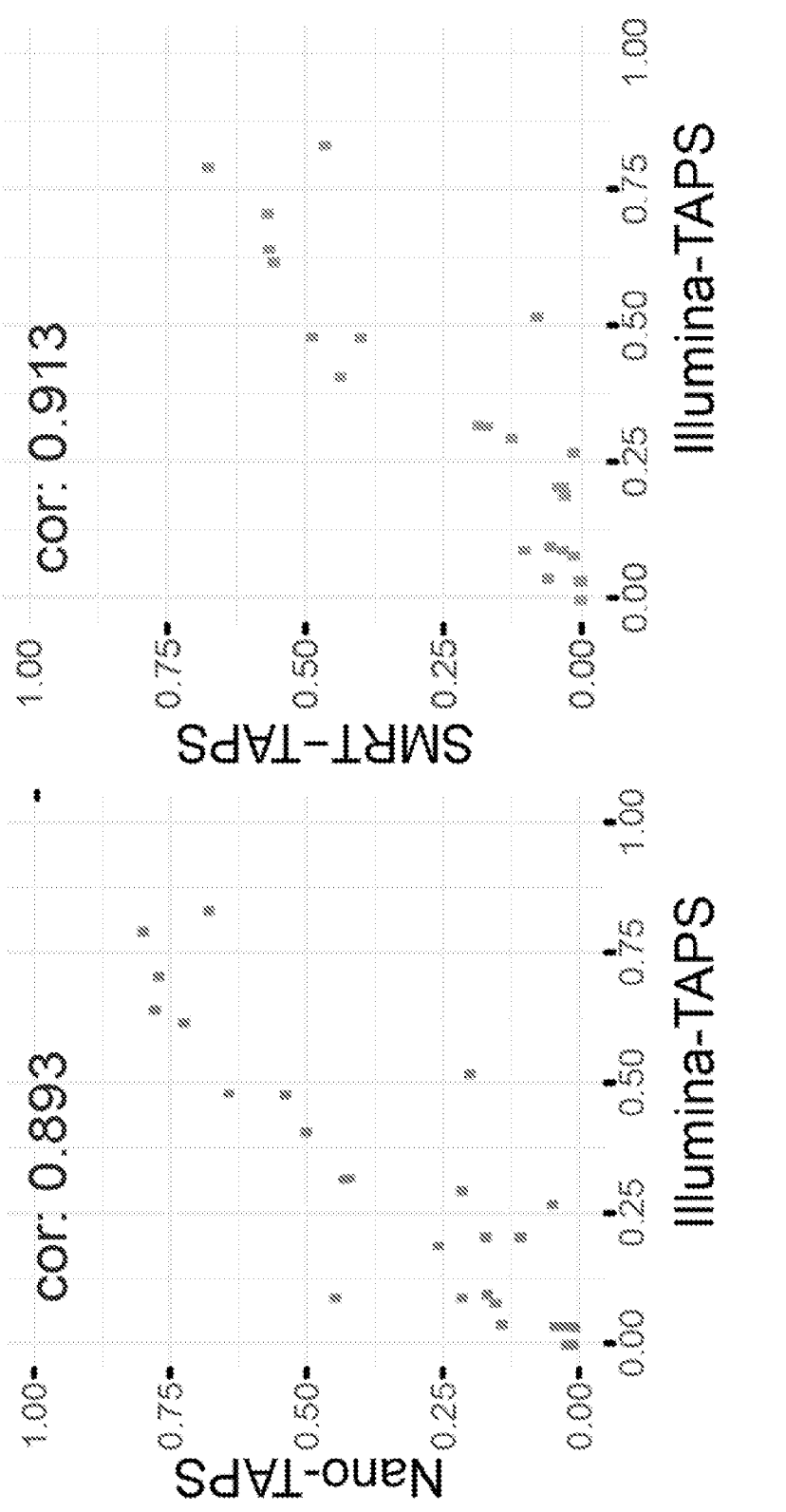
FIG. 7 provides a scatter plot showing the correlation of methylation detected by Nano-TAPS, SMRT-TAPS, and Illumina-TAPS on the ~4 kb mESC genomic region shown in FIG. 5, with correlation coefficient listed at the top of each plot. CG sites with Illumina sequencing depth >8× were selected for correlation analysis.

Applying the previously reported TAPS method (see PCT Publication No. WO2019/136413, which is herein incorporated by reference in its entirety) to the model DNA resulted in gaps in the methylation analysis of the mESC DNA (FIG. 5). Both Nano-TAPS and SMRT-TAPS detected methylated CpG sites in the gap, which contains Hba-a1 (encoding hemoglobin alpha, adult chain 1), a previously unmappable gene that has an identical sequence to its homolog Hba-a2 (encoding hemoglobin alpha, adult chain 2) (FIGS. 5 and 6). Across the 4 kb region (outside of the gap), Nano-TAPS and SMRT-TAPS showed good correlation with Illumina-TAPS at CpG sites with sequencing depth>8 (Pearson correlation coefficient 0.893 and 0.913, respectively, FIG. 7) confirming that lrTAPS provides comparable results to Illumina sequencing of biological samples. The differences are most likely explained by the relatively low coverage of Illumina-TAPS (average depth 17× in this region) compared to the high coverage targeted sequencing of Nano-TAPS (14,600×) and SMRT-tlTAPS (210,100×). This demonstrated the power of lrTAPS to provide accurate DNA methylation maps of previously inaccessible non-unique genomic regions.

Example 5: lrTAPS is Suitable for the Study of Methylation Pattern in Clinically Relevant, Biological Samples To further evaluate the utility of lrTAPS analysis of biological samples, the method was applied to study hepatitis B virus (HBV) DNA methylation.

HBV is a global health problem with more than 250 million people chronically infected and at least 880,000 deaths/year from liver diseases. HBV replicates via a 3.2 kb episomal copy of its genome, known as covalently closed circular DNA (cccDNA), and gene transcription is regulated by DNA methylation and other epigenetic modifications. A linear form of HBV DNA can be generated during viral replication that can integrate into the host genome; these integrated viral DNA fragments may contribute to carcinogenesis. However, the understanding of the role DNA methylation plays in the HBV life cycle and associated pathogenesis is limited by the insensitivity of BS-seq or methylation-specific PCR to quantify the HBV DNA methylation status.

Figure 8:
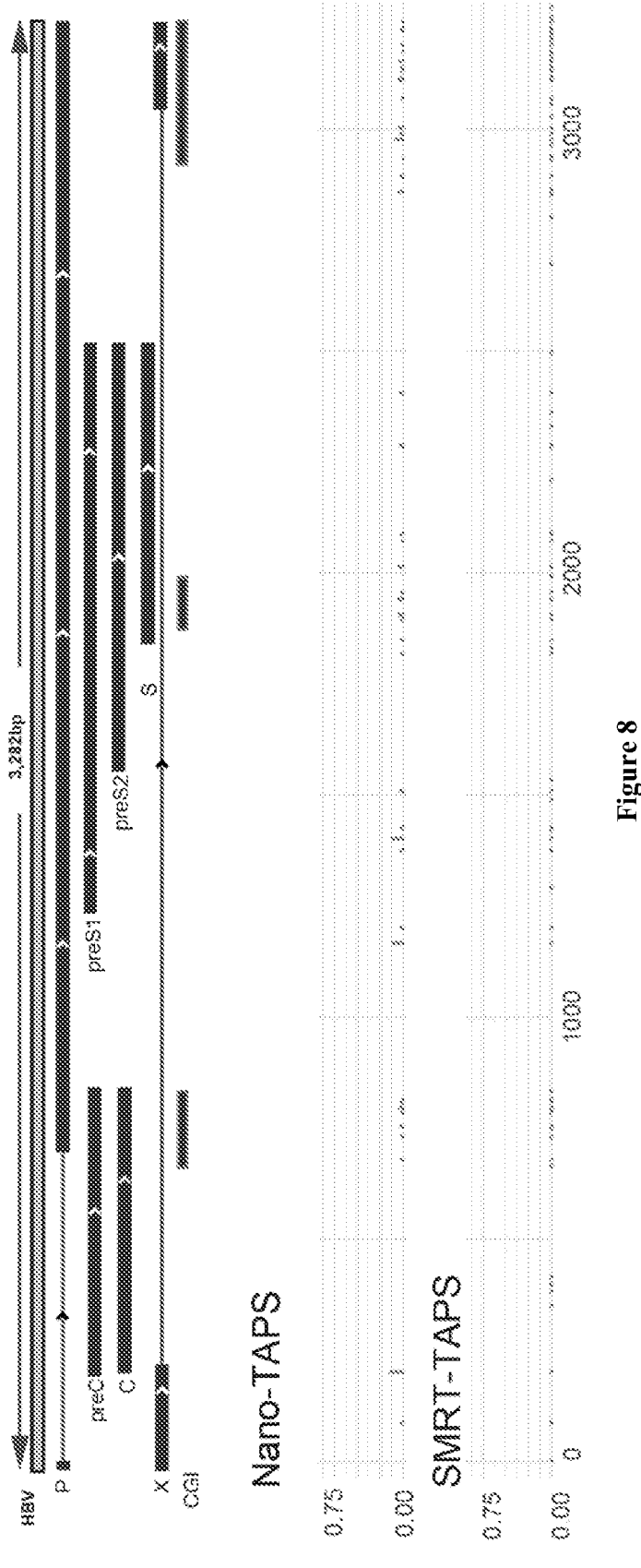
FIG. 8 illustrates CpG methylation in HBV cccDNA isolated from infected HepG2-NTCP cells (6 days post-infection) detected by Nano-TAPS and SMRT-TAPS.
Figure 9:
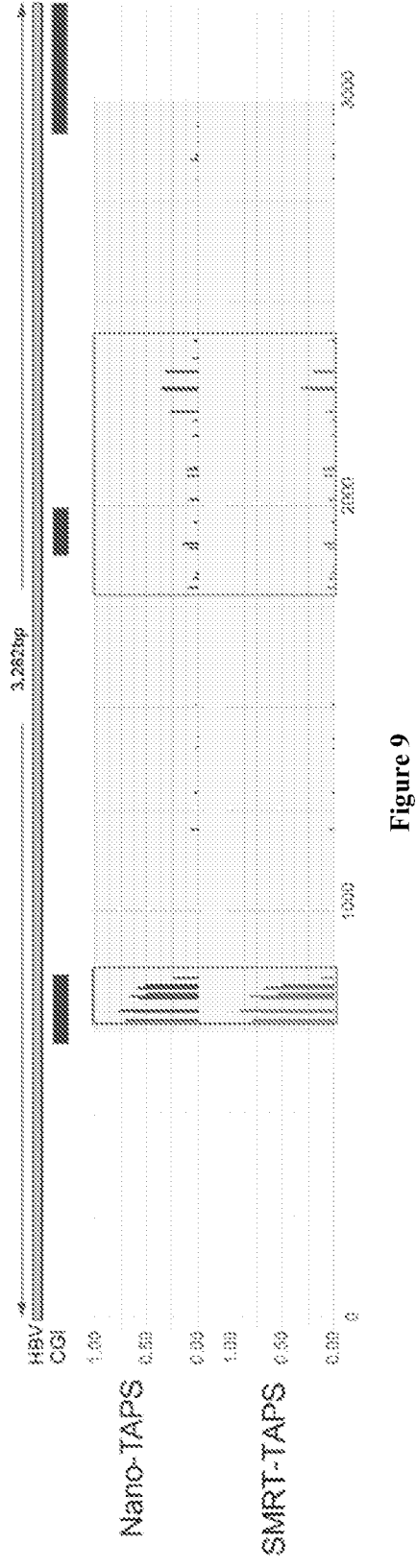
FIG. 9 illustrates CpG methylation of integrated HBV DNA in Huh-1 cells detected by Nano-TAPS and SMRT-TAPS. The shaded area shows the covered regions with lrTAPS. Regions of methylated CpGs are indicated by the boxes.

Using lrTAPS, it could be shown for the first time that HBV cccDNA in de novo infected HepG2-NTCP (HepG2 cells engineered to express sodium taurocholate co-transporting polypeptide (NTCP) which support the full HBV life cycle) is unmethylated (FIG. 8), consistent with active transcription and genesis of infectious particles. In contrast, integrated copies of HBV DNA in Huh-1 hepatoma cells are methylated at the predicted CpG islands (CGI) and gene body (FIG. 9).

Example 6: lrTAPS is Useful for Phasing Long-Range Epigenetic Variations at Single Molecule-Level Another major benefit of lrTAPS is the ability to phase long-range epigenetic variations at single molecule-level.

Figure 10:
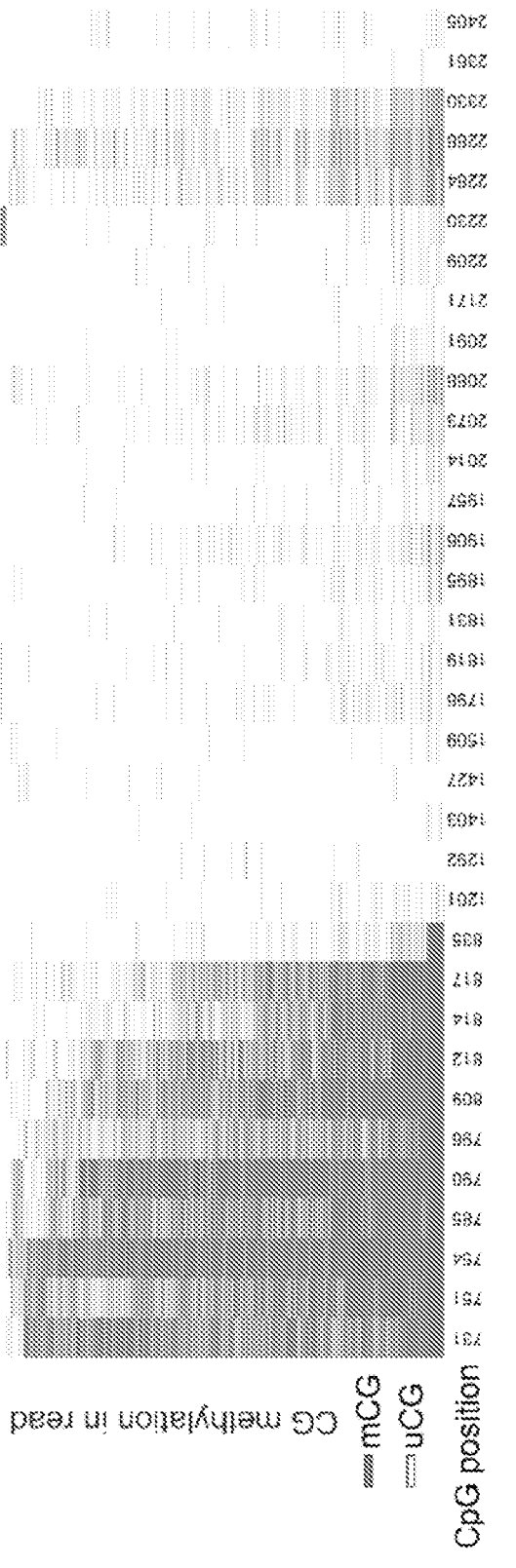
FIG. 10 shows a heatmap showing integrated HBV DNA methylation in each SMRT read (34,755 reads were included). Reads were ranked by the average methylation in the first CpG Island. The blue bar indicates the methylated CpG while white bar indicates un-methylated CpG. The number in the bottom indicates the relative position of CpG in the genome.
Figure 11:
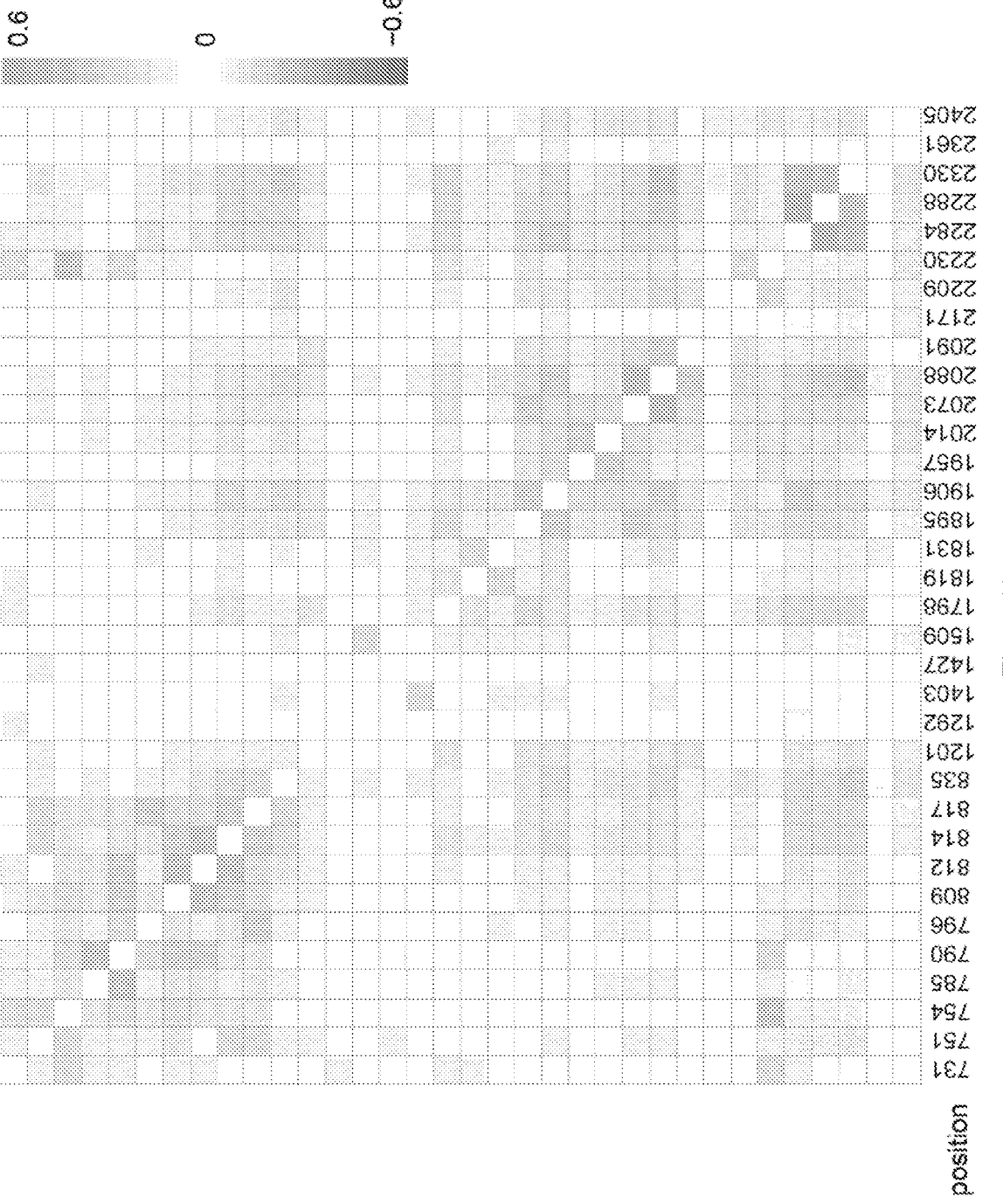
FIG. 11 shows a heatmap illustrating the Pearson's correlation of methylation in each CpG sites measured by SMRT-TAPS in HBV integrated DNA in Huh-1 cells. The methylation status for selected CpG sites in each read was designated to 0 for un-methylated CpG and 1 for methylated CpG as shown in FIG. 10. The correlation of methylation status between these CpG sites is calculated with the cor function in R.

Further analysis of the methylation at the level of single long reads shows distinct methylation events on the HBV genome that are either correlated or anti-correlated over long distances, indicating heterogeneity of DNA methylation status among integrated HBV DNA (FIGS. 10 and 11). Such feature could only be uncovered with the phased methylome delivered by long-read sequencing and is important for studying heterogeneous samples such as patient derived material.

An overview nucleic sequences can be found in Table 4.

TABLE 4

| | Nucleic acid sequences | |
|---|---|---|
| Description | Sequence | SEQ ID NO: |
| Forward primer | ACTGGAACAACACTCAACCCTA | 1 |
| Reverse primer | AGGGTGGTGAATGTGAAACC | 2 |
| Primer 4 kb-F | CATCGAGCATCAAATGAAACTGC | 3 |
| Primer 4 kb-R | ACGTTATACGATGTCGCAGAGT | 4 |
| Primer 4 kb-F-BstAPI | ATCAGGTGGCACACTCTATCTCGGAAGCAGACTCTGCC ATCGAGCATCAAATGAAACTGC | 5 |
| Primer Lambda-F1 | CTTCGGCCTGTGTCAGTTCT | 6 |
| Primer Lambda-F2 | AACGTCTCTTCAGGCCACTG | 7 |
| Primer Lambda-F3 | ATCGCACCATCAGCCAGAAA | 8 |
| Primer Lambda-F4 | GGTGTGGCAAAGCTTGAAGG | 9 |
| Primer Lambda-F5 | CTTACCCAACCCACCTGGTC | 10 |
| Primer Lambda-R1 | CGGATATCCCACAGGTGAGC | 11 |
| Primer Lambda-R2 | GCTCAGTTTGGGTTGTGCTG | 12 |
| Primer Lambda-R3 | CCATGCGCTTGCTCTTCATC | 13 |
| Primer Chr11-F | ACGCCCTTGGAGGGCATA | 14 |
| Primer Chr11-R | AGGGCATGGGTGGAGACTAT | 15 |
| Primer Chr13-F | TTAGCTGCACCTTTGTGCTT | 16 |
| Primer Chr13-R | TTGCACCCTGTCTGCAATCT | 17 |
| Primer ApaLI-F | CACGTCGCATGGAGACCAC | 18 |
| Primer ApaLI-R | CCGGCAGATGAGAAGGaACAG | 19 |
| Primer HepB8F | CTTATAGACCACCAAATGCCCCTA | 20 |
| Primer HepB22R | CAAAACAAGCGGCTAGGAGTTC | 21 |
| Illumina adapter | ACACTCTTTCCCTACACGACGCTCTTCCGATCT | 22 |
| Illumina adapter | 5Phos/GATCGGAAGAGCACACGTCT | 23 |
| Modified SMRTbell adaptor | 5Phos/GTAGTCTCGCACAGATATCTCTCTTTTCCTCCT CCTCCGTTGTTGTTGTTGAGAGAGATATCTGTGCGAGA CTACAGT | 24 |

We claim:

1. A method for chemically modifying a nucleic acid sample, comprising the steps of:
   (a) converting 5-methyl cytosine (5mC) and/or 5-hydroxymethylcytosine (5hmC) in a nucleic acid sample comprising a target nucleic acid to 5-carboxylcytosine (5caC) and/or 5-formylcytosine (5fC) with a TET enzyme; and
   (b) converting 5caC and/or 5fC in the nucleic acid sample to dihydrouracil (DHU) with a borane reducing reagent to provide a modified nucleic acid sample comprising a modified target nucleic acid; wherein steps (a) and (b) are performed in a single reaction vessel without a purification step between steps (a) and (b); and wherein the modified target nucleic acid has a length of from 3 kb to 10 kb.

2. The method of claim 1, further comprising providing a quantitative level of 5mC or 5hmC at each location in the target nucleic acid using the percentages of a DHU or T at each transition location.

3. The method of claim 1, wherein the method further comprises inactivating the TET enzyme by providing a protease, by a change in temperature, and/or by a change in pH.

4. The method of claim 3, wherein the protease is proteinase K.

5. The method of claim 1, wherein the method further comprises the step of amplifying the copy number of the modified target nucleic acid.

6. The method of claim 1, wherein the borane reducing agent is selected from the group consisting of pyridine borane, 2-picoline borane (pic-$BH_3$), borane, sodium borohydride, sodium cyanoborohydride, and sodium triacetoxyborohydride.

7. The method of claim 1, further comprising adding a glucose blocking group to the 5hmC in the nucleic acid sample prior to converting 5mC and/or 5hmC in the nucleic acid sample to 5caC and/or 5fC.

8. The method of claim 7, wherein the step of adding a glucose blocking group to the 5hmC is done in the same tube as the step of converting 5mC and/or 5hmC in the nucleic acid sample to 5caC and/or 5fC, and wherein the method is performed without a purification step between the step of adding a glucose blocking group to the 5hmC and the step of converting 5mC and/or 5hmC in the nucleic acid sample to 5caC and/or 5fC.

9. A method for determining a whole genome methylome, comprising the steps of:

(a) converting 5-methyl cytosine (5mC) and/or 5-hydroxymethylcytosine (5hmC) in a nucleic acid sample comprising a whole genomic DNA of a cell to 5-carboxylcytosine (5caC) and/or 5-formylcytosine (5fC) with a ten eleven translocation (TET) enzyme; and (b) converting 5caC and/or 5fC in the nucleic acid sample to dihydrouracil (DHU) with a borane reducing reagent to provide a modified whole genomic DNA; and (c) amplifying and sequencing target nucleic acid sequences ranging from 3 kb to 10 kb in length;

wherein steps (a) and (b) are performed in a single reaction vessel without a purification step between steps (a) and (b).

10. The method of claim 9, wherein said nucleic acid sample comprises less than or equal to about 100 ng of said whole genomic DNA.

11. The method of claim 9, wherein the whole genomic DNA comprises a plurality of unmodified cytosines.

12. The method of claim 9, wherein the method further comprises identifying the location of said 5mC or said 5hmC in said modified whole genomic DNA comprising detecting the presence of DHU in the modified whole genomic DNA, or converting the DHU to thymine (T) and detecting the presence of the thymine (T) in the modified whole genomic DNA; and wherein a cytosine (C) to DHU transition or a cytosine (C) to thymine (T) transition in the modified whole genomic DNA compared to the whole genomic DNA provides the location of a 5mC or 5hmC in the whole genomic DNA.

13. The method of claim 9, wherein the method further comprises converting said DHU to thymine (T).

* * * * *

SEQUENCE LISTING

<160> NUMBER OF SEQ ID NOS: 26

<210> SEQ ID NO 1
<211> LENGTH: 22

```
<212> TYPE: DNA
<213> ORGANISM: Artificial Sequence
<220> FEATURE:
<223> OTHER INFORMATION: Primer

<400> SEQUENCE: 1
actggaacaa cactcaaccc ta                                                    22

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agggtggtga atgtgaaacc                                                       20

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
catcgagcat caaatgaaac tgc                                                   23

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
acgttatacg atgtcgcaga gt                                                    22

<210> SEQ ID NO 5
<211> LENGTH: 60
<212> TYPE: DNA
<213> ORGANISM: Artificial Sequence
<220> FEATURE:
<223> OTHER INFORMATION: Primer

<400> SEQUENCE: 5
atcaggtggc acactctatc tcggaagcag actctgccat cgagcatcaa atgaaactgc          60

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cttcggcctg tgtcagttct                                                       20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
```

-continued

```
aacgtctctt caggccactg                                                    20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
atcgcaccat cagccagaaa                                                    20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggtgtggcaa agcttgaagg                                                    20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cttacccaac ccacctggtc                                                    20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cggatatccc acaggtgagc                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gctcagtttg ggttgtgctg                                                    20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccatgcgctt gctcttcatc                                                    20

<210> SEQ ID NO 14
<211> LENGTH: 18
<212> TYPE: DNA
<213> ORGANISM: Artificial Sequence
```

-continued

```
<220> FEATURE:
<223> OTHER INFORMATION: Primer

<400> SEQUENCE: 14
acgcccttgg agggcata                                                18

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
agggcatggg tggagactat                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ttagctgcac ctttgtgctt                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ttgcaccctg tctgcaatct                                              20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
cacgtcgcat ggagaccac                                               19

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
ccggcagatg agaaggaaca g                                            21

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
cttatagacc accaaatgcc ccta                                         24
```

-continued

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
caaaacaagc ggctaggagt tc                                              22

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
acactctttc cctacacgac gctcttccga tct                                  33

<210> SEQ ID NO 23
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(1)
<223> OTHER INFORMATION: phosphorylated

<400> SEQUENCE: 23
gatcggaaga gcacacgtct                                                 20

<210> SEQ ID NO 24
<211> LENGTH: 80
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(1)
<223> OTHER INFORMATION: phosphorylated

<400> SEQUENCE: 24
gtagtctcgc acagatatct ctctcttttc ctcctcctcc gttgttgttg ttgagagaga     60
tatctgtgcg agactacagt                                                 80

<210> SEQ ID NO 25
<211> LENGTH: 815
<212> TYPE: DNA
<213> ORGANISM: Mus musculus

<400> SEQUENCE: 25
gacacttctg attctgacag actcaggaag aaaccatggt gctctctggg gaagacaaaa     60
gcaacatcaa ggctgcctgg gggaagattg gtggccatgg tgctgaatat ggagctgaag    120
ccctggaaag gtgagaacag gaccttgatc tgtaaggatc acaggatcca atatggacct    180
ggcactcgct cagtgggcag cttctaacta tgctttttctg tgacctcaac ttctcttctc    240
tccttctccc aggatgtttg ctagcttccc caccaccaag acctacttcc ctcactttga    300
tgtaagccac ggctctgccc aggtcaaggg tcacggcaag aaggtcgccg atgctctggc    360
caatgctgca ggccacctcg atgacctgcc cggtgccctg tctgctctga gcgacctgca    420

-continued

```
tgcccacaag ctgcgtgtgg atcccgtcaa cttcaaggta tgcgctggga cctggcaggc      480
ggcatctggg acccctagga agggcttggg ggtcctcgtg cccaaggcag ggaacatagt      540
ggtcccagga aggggagcag aggcatcagg gtgtccactt tgtctccgca gctcctgagc      600
cactgcctgc tggtgacctt ggctagccac caccctgccg atttcacccc cgcggtgcat      660
gcctctctgg acaaattcct tgcctctgtg agcaccgtgc tgacctccaa gtaccgttaa      720
gctgccttct gcggggcttg ccttctggcc atgcccttct tctctccctt gcacctgtac      780
ctcttggtct ttgaataaag cctgagtagg aagaa                                  815

<210> SEQ ID NO 26
<211> LENGTH: 819
<212> TYPE: DNA
<213> ORGANISM: Mus musculus

<400> SEQUENCE: 26
acttctgatt ctgacagact caggaagaaa ccatggtgct ctctggggaa gacaaaagca       60
acatcaaggc tgcctggggg aagattggtg gccatggtgc tgaatatgga gctgaagccc      120
tggaaaggtg agaacaggac cttgatctgt aaggatcaca ggatccaata tggacctggc      180
actcgctcag tgggcagctt ctaactatgc ttttctgtga cctcaacttc tcttctctcc      240
ttctcccagg atgtttgcta gcttccccac caccaagacc tacttccctc actttgatgt      300
aagccacggc tctgcccagg tcaagggtca cggcaagaag gtcgccgatg ctctggccaa      360
tgctgcaggc cacctcgatg acctgcccgg tgccctgtct gctctgagcg acctgcatgc      420
ccacaagctg cgtgtggatc ccgtcaactt caaggtatgc gctgggacct ggcaggcggc      480
atctgggacc cctaggaagg gcttgggggt cctcgtgccc aaggcaggga acatagtggt      540
cccaggaagg ggagcagagg catcagggtg tccactttgt ctccgcagct cctgagccac      600
tgcctgctgg tgaccttggc tagccaccac cctgccgatt tcaccccgc ggtgcatgcc       660 tctctggata aattccttgc ctctgtgagc accgtgctga cctccaagta ccgttaagct      720
gccttctgcg gggcttgcct tctggccatg cccttcttct ctcccttgca cctgtacctc      780
ttggtctttg aataaagcct gagtaggaag aagcctgca                              819
```